US011696740B2

(12) United States Patent
Dickie et al.

(10) Patent No.: US 11,696,740 B2
(45) Date of Patent: *Jul. 11, 2023

(54) METHOD AND SYSTEM FOR DEFINING CUT LINES TO GENERATE A 3D FETAL REPRESENTATION

(71) Applicant: Clarius Mobile Health Corp., Vancouver (CA)

(72) Inventors: Kris Dickie, Vancouver (CA); Laurent Pelissier, North Vancouver (CA); Parisa Asgharzadeh, Vancouver (CA)

(73) Assignee: Clarius Mobile Health Corp., Vancouver (CA)

(*) Notice: Subject to any disclaimer, the term of this patent is extended or adjusted under 35 U.S.C. 154(b) by 0 days.

This patent is subject to a terminal disclaimer.

(21) Appl. No.: 17/959,228

(22) Filed: Oct. 3, 2022

(65) Prior Publication Data

US 2023/0027135 A1 Jan. 26, 2023

Related U.S. Application Data

(63) Continuation of application No. 16/995,712, filed on Aug. 17, 2020, now Pat. No. 11,457,891.

(51) Int. Cl.
*A61B 8/08* (2006.01)
*A61B 8/00* (2006.01)

(52) U.S. Cl.
CPC ......... *A61B 8/0866* (2013.01); *A61B 8/466* (2013.01); *A61B 8/523* (2013.01)

(58) Field of Classification Search
CPC ........ A61B 8/0866; A61B 8/466; A61B 8/523
See application file for complete search history.

(56) References Cited

U.S. PATENT DOCUMENTS

| 8,121,305 | B2 | 2/2012 | Servello et al. |
| 10,198,832 | B2* | 2/2019 | De Fauw ............. G06T 7/0012 |
| 10,825,168 | B2* | 11/2020 | Tegzes ..................... G06T 7/11 |
| 11,457,891 | B2 | 10/2022 | Dickie et al. |
| 2005/0240104 | A1 | 10/2005 | Shim et al. |

(Continued)

FOREIGN PATENT DOCUMENTS

| WO | 2018127497 | 7/2018 |
| WO | 2020045987 | 3/2020 |

OTHER PUBLICATIONS

Machine translation of PCT Patent Application No. WO2020045987A1 entitled "System and method for providing deep learning-based virtual reality 3d embryo model".

(Continued)

*Primary Examiner* — Rochelle D Turchen
(74) *Attorney, Agent, or Firm* — Julian Ho; Susan Ben-Oliel

(57) ABSTRACT

A plurality of ultrasound frames of a fetus are acquired using an ultrasound scanner, which may be oriented arbitrarily with respect to the fetus during the acquisition. The ultrasound frames are processed against an artificial intelligence model to predict a different cut line on each of the ultrasound frames. Each cut line is predicted to be exterior to an image of the fetus appearing on the ultrasound frame. The different cut lines on the plurality of ultrasound frames are then used to identify ultrasound data in the image frames to generate a 3D representation of the fetus.

20 Claims, 7 Drawing Sheets

(56) References Cited

U.S. PATENT DOCUMENTS

| | | | |
|---|---|---|---|
| 2007/0167760 A1 | 7/2007 | Kim et al. | |
| 2011/0066031 A1 | 3/2011 | Lee et al. | |
| 2012/0046549 A1 | 2/2012 | Kim et al. | |
| 2012/0087561 A1* | 4/2012 | Guetter | G06T 7/174 |
| | | | 382/131 |
| 2014/0161329 A1* | 6/2014 | Tizhoosh | G06T 7/149 |
| | | | 382/128 |
| 2015/0279086 A1* | 10/2015 | Ogino | A61B 8/469 |
| | | | 345/424 |
| 2016/0242742 A1* | 8/2016 | Gratacós | G06V 20/695 |
| 2017/0251999 A1 | 9/2017 | Noguchi et al. | |
| 2019/0057505 A1* | 2/2019 | Pheiffer | G06T 7/0016 |
| 2019/0087939 A1* | 3/2019 | Hakimuddin | G06V 10/82 |
| 2019/0117186 A1 | 4/2019 | Klinder et al. | |
| 2019/0340752 A1* | 11/2019 | Brestel | G06V 10/764 |
| 2020/0043170 A1* | 2/2020 | Ravishankar | G06T 7/10 |
| 2020/0113542 A1* | 4/2020 | Perrey | A61B 8/5207 |
| 2020/0155114 A1* | 5/2020 | Park | A61B 8/0883 |
| 2020/0202551 A1* | 6/2020 | Ciofolo-Veit | A61B 8/5223 |
| 2020/0234435 A1* | 7/2020 | Raynaud | G06T 5/006 |
| 2020/0234461 A1* | 7/2020 | Osumi | G06T 7/62 |
| 2020/0265579 A1* | 8/2020 | Schmidt-Richberg | |
| | | | G16H 50/20 |
| 2020/0279411 A1* | 9/2020 | Atria | G06T 11/006 |
| 2020/0281570 A1* | 9/2020 | Sato | G01S 7/52038 |
| 2020/0337626 A1* | 10/2020 | Wang | A61B 5/7267 |
| 2021/0059796 A1* | 3/2021 | Weiss | G06N 3/08 |
| 2022/0047241 A1 | 2/2022 | Dickie et al. | |

OTHER PUBLICATIONS

Yang et al., Towards Automatic Semantic Segmentation in Volumetric Ultrasound, 2017, Springer International Publishing, MICCAI 2017, Part I, LNCS 10433, pp. 711-719 (Year: 2017).

Wang et al., Deep Learning in Medical Ultrasound Image Segmentation: a Review, Feb. 25, 2020, arxiv:2022.07703v2 (Year: 2020).

Chen et al., Automatic Fetal Ultrasound Standard Plane Detection Using Knowledge Transferred Recurrent Neural Networks, 2015, Springer International Publishing Switzerland, MICCAI 2015, Part 1, LNCS 9349, pp. 507-514 (Year 2015).

Liu et al., Deep Learning in Medical Ultrasound Analysis: A Review, Jan. 2019, Elsevier, Engineering 5, 261-275 (Year: 2019).

* cited by examiner

METHOD AND SYSTEM FOR DEFINING CUT LINES TO GENERATE A 3D FETAL REPRESENTATION

CROSS-REFERENCE TO RELATED APPLICATION

This application is a continuation of U.S. patent application Ser. No. 16/995,712, filed Aug. 17, 2020. The entire contents of U.S. patent application Ser. No. 16/995,712 are hereby incorporated by reference.

TECHNICAL FIELD

This disclosure relates to ultrasound imaging. In particular, it relates to systems and methods for generating a three dimensional (3D) fetal representation.

BACKGROUND

Ultrasound is a useful, non-invasive imaging technique capable of producing real time images of internal structures within tissue. Ultrasound imaging has an advantage over X-ray imaging in that ultrasound imaging does not involve ionizing radiation. Some mobile ultrasound scanners, including app-based ultrasound scanners, communicate with an add-on device that can act as both as a display and a control device. Examples of these add-on devices are mobile phones, tablets, laptops or desktop computers.

When using some ultrasound scanners (whether mobile or not) for generating a 3D fetal representation, users are traditionally expected to orientate the ultrasound scanner to provide an image of the midsaggital plane of the fetus. They are then expected to define a region of interest and/or a cut line on a frame of this two dimensional (2D) ultrasound image. The cut line defines a portion of the ultrasound frame that excludes the fetus, and which is removed for generating the 3D representation. The same cut line is then used on multiple 2D ultrasound frame slices, which are subsequently acquired while holding the ultrasound scanner in a still position or as the ultrasound scanner sweeps across the skin surface.

Some ultrasound scanning systems allow 4D ultrasound representations to be obtained, in which a 3D representation is obtained repeatedly so that the fetus can be viewed in 3D in real time.

A skilled ultrasound operator is required, first to obtain the midsaggital plane, and then to define a suitable cut line on the ultrasound frame. Furthermore, use of the same cut line for the multiple 2D image slices may cause imperfections to be introduced when generating the 3D representation. For example, a cut line that accurately excluded non-fetus anatomy (e.g., the umbilical cord or placenta) in the 2D ultrasound frame on which the cut line was defined may inadvertently include such non-fetus anatomy on another 2D ultrasound frame. This may lead to the non-fetus anatomy being included in the generated 3D representation, and the non-fetus anatomy obscuring the fetus in the generated 3D representation. In another example, the cut line that accurately included all fetus anatomy in the 2D ultrasound frame on which the cut line was defined may inadvertently exclude portions of the fetus on another 2D ultrasound frame. This may lead to the resulting 3D representation being incomplete (e.g., omitting a limb or a portion of the head of the fetus). Furthermore, movement of the fetus during the scan may also lead to imperfections in the generated 3D representation. In these various examples, the whole process may need to be repeated. It would therefore be useful to find a way to reduce the required skill level of the operator and to provide improved cut lines on the multiple 2D images that are used to generate the 3D representation of the fetus.

The above background information is provided to reveal information believed by the applicant to be of possible relevance to the present invention. No admission is necessarily intended, nor should be construed, that any of the preceding information constitutes prior art against the present invention. The embodiments discussed herein may address and/or ameliorate one or more of the aforementioned drawbacks identified above. The foregoing examples of the related art and limitations related thereto are intended to be illustrative and not exclusive. Other limitations of the related art will become apparent to those of skill in the art upon a reading of the specification and a study of the drawings herein.

BRIEF DESCRIPTION OF DRAWINGS

The following drawings illustrate embodiments of the invention and should not be construed as restricting the scope of the invention in any way.

DETAILED DESCRIPTION

A. Glossary

Figure 1:
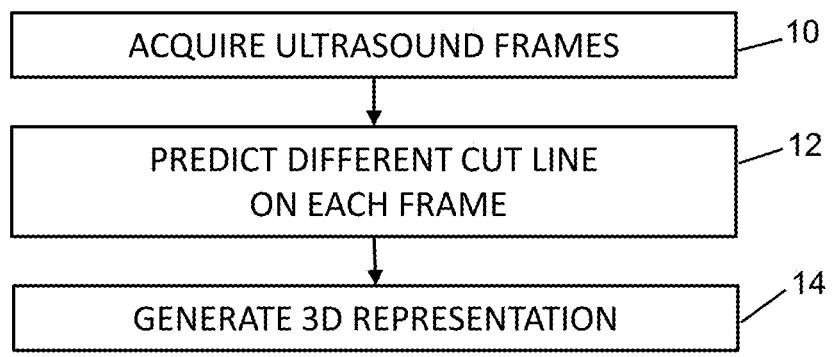
FIG. 1 is a flowchart of the main steps for generating a 3D fetal representation, according to an embodiment of the present invention.

The term "AI model" means a mathematical or statistical model that may be generated through artificial intelligence techniques such as machine learning and/or deep learning. For example, these techniques may involve inputting labeled or classified data into a neural network algorithm for training, so as to generate a model that can make predictions or decisions on new data without being explicitly programmed to do so. Different software tools (e.g., TensorFlow™, PyTorch™, Keras™) may be used to perform machine learning processes.

The term "module" can refer to any component in this invention and to any or all of the features of the invention without limitation. A module may be a software, firmware or hardware module, and may be located, for example, in the ultrasound scanner, a display device or a server.

The term "communications network" can include both a mobile network and data network without limiting the term's meaning, and includes the use of wireless (e.g. 2G, 3G, 4G, 5G, WiFi™, WiMAX™, Wireless USB (Universal Serial Bus), Zigbee™, Bluetooth™ and satellite), and/or hard wired connections such as local, internet, ADSL (Asymmetrical Digital Subscriber Line), DSL (Digital Subscriber Line), cable modem, T1, T3, fiber-optic, dial-up modem, television cable, and may include connections to flash memory data cards and/or USB memory sticks where appropriate. A communications network could also mean dedicated connections between computing devices and electronic components, such as buses for intra-chip communications.

The term "operator" (or "user") may refer to the person that is operating an ultrasound scanner (e.g., a clinician, medical personnel, a sonographer, ultrasound student, ultrasonographer and/or ultrasound technician).

The term "processor" can refer to any electronic circuit or group of circuits that perform calculations, and may include, for example, single or multicore processors, multiple processors, an ASIC (Application Specific Integrated Circuit), and dedicated circuits implemented, for example, on a reconfigurable device such as an FPGA (Field Programmable Gate Array). A processor may perform the steps in the flowcharts and sequence diagrams, whether they are explicitly described as being executed by the processor or whether the execution thereby is implicit due to the steps being described as performed by the system, a device, code or a module. The processor, if comprised of multiple processors, may be located together or geographically separate from each other. The term includes virtual processors and machine instances as in cloud computing or local virtualization, which are ultimately grounded in physical processors.

The term "scan convert", "scan conversion", or any of its grammatical forms refers to the construction of an ultrasound media, such as a still image or a video, from lines of ultrasound scan data representing echoes of ultrasound signals. Scan conversion may involve converting beams and/or vectors of acoustic scan data which are in polar (R-theta) coordinates to cartesian (X-Y) coordinates.

The term "system" when used herein, and not otherwise qualified, refers to a system for generating a 3D fetal representation, the system being a subject of the present invention. In various embodiments, the system may include an ultrasound machine (including a display and one or more transducers); an ultrasound scanner and a display device; and/or an ultrasound scanner, display device and a server.

The term "ultrasound image frame" (or "image frame" or "ultrasound frame") refers to a frame of post-scan conversion data that is suitable for rendering an ultrasound image on a screen or other display device.

B. Exemplary Embodiments

At a high level, the embodiments herein generally allow ultrasound frames of a fetus to be acquired using an ultrasound scanner, which may be oriented arbitrarily with respect to the fetus during the acquisition. The ultrasound frames may be processed against an artificial intelligence (AI) model to predict a suitable cut line on each of the ultrasound frames, where each cut line is positioned exterior to an image of the fetus appearing on the ultrasound frame. The different cut lines on the ultrasound frames are then used to generate a 3D representation of the fetus.

Referring to FIG. 1, the high-level steps of a method for generating a 3D fetal representation are shown. In step 10, a number of ultrasound frames of the fetus may be acquired using an ultrasound scanner (hereinafter "scanner", "probe", or "transducer" for brevity). The ultrasound frames may be acquired by fanning a series of a planes (with a frame each containing a sequence of transmitted and received ultrasound signals), through an angle and capturing a different ultrasound frame at each of a number of different angles. During the scanning, the scanner may be held steady by an operator of the scanner while a motor in the head of the scanner tilts the ultrasonic transducer to acquire ultrasound frames at different angles. Additionally or alternatively, other methods of acquiring a series of ultrasound frames may be employed, such as using a motor to translate (e.g., slide) the ultrasonic transducer or rotate it, or manually tilting, translating or rotating the ultrasound scanner. When acquiring the number of ultrasound frames, it is possible, but not necessary, to initially place the scanner in the midsagittal plane of the fetus. In the examples discussed below with respect to FIGS. 2-4, example embodiments are discussed where the AI model is trained with (and correspondingly, predict) cut lines on a midsagittal plane view of the fetus.

In various embodiments, the AI model may additionally be trained with cut lines on different views of the fetus. For example, these different views may include coronal and/or transverse plane views of the fetus, including views from different angles that combine any of a sagittal plane view, a coronal plane view, or a transverse plane view. In these embodiments where the AI model is also trained to predict cut lines on these different views, the scanner may be placed in an arbitrary orientation with respect to the fetus, provided that the scanner captures at least a portion of the fetus. Additional discussion related to the different fetal ultrasound frames that can used for training the AI model is provided below in relation to FIG. 7.

In step 12, a different cut line is predicted on each of the acquired ultrasound frames, where possible. To do this, each ultrasound frame may be processed against an AI model to predict the respective cut line. The cut lines may be predicted without the operator of the scanner needing to manually input a region of interest on an ultrasound frame. As each ultrasound frame may have a different image of the fetus, or portion of the fetus, then the optimal cut line may vary in position and from frame to frame. The cut lines are predicted by the AI model to be exterior to an image of the fetus in the ultrasound frames.

In step 14, the different cut lines on the ultrasound frames are then used to eliminate various non-fetal anatomy from each of the ultrasound frames. The remaining image data can be used as slices that together, generate a 3D representation of the fetus. Additional details about how step 14 of FIG. 1 can be performed are discussed below.

Figure 2:
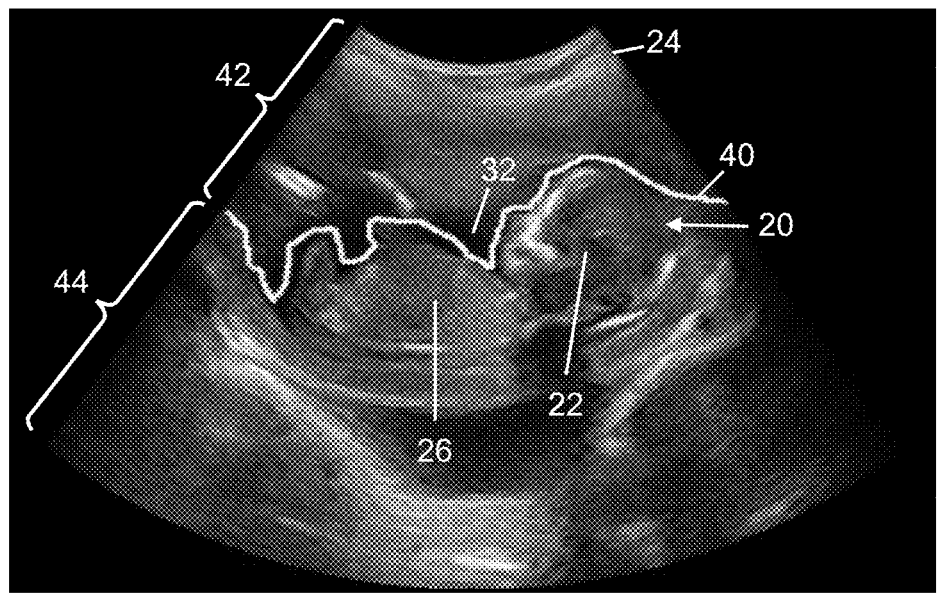
FIG. 2 is a fetal ultrasound image showing a cut line, according to an embodiment of the present invention.

Referring to FIG. 2, an ultrasound image of a fetus 20 is shown. The fetus 20 may include the fetal head 22 and fetal abdomen 26. Other anatomy may also be visible in fetal ultrasound frames. For example, this anatomy may include the uterus, uterine wall, the placenta, the amniotic sac, the umbilical cord, and the amniotic fluid 32. FIG. 2 illustrates an example cut line 40 as may initially be used to train an AI model, or as may be predicted by an AI model. In the illustrated example, the cut line 40 is shown exterior to the fetus 20 and interior to (e.g., inside) an imaged uterus that surrounds the fetus 20.

The cut line 40 may closely follow the profile of the fetus 20. Depending on the profile of the fetus 20 viewable in a given ultrasound frame, the nature of the cut line may vary. For example, since the profile of the fetus 20 viewable in the ultrasound frame is non-smooth, with various protrusions for the head or limbs, the corresponding cut line 40 may correspondingly be uneven and non-smooth so that the cut line 40 contours close to the fetal head 22 (on the right side of the image), and the fetal abdomen 26 (in the middle of the image).

In other ultrasound frames, if the profile of the fetus 20 appearing on these other ultrasound frames have fewer or more protrusions and/or indentations, the corresponding cut lines may be smoother or more complex than example cut line 40 shown in FIG. 2. Additionally or alternatively, in still other ultrasound frames, the predicted cut line may be closer or further from the fetus 20 than the predicted cut line 40, in one or more different regions of the cut line 40.

Figure 3:
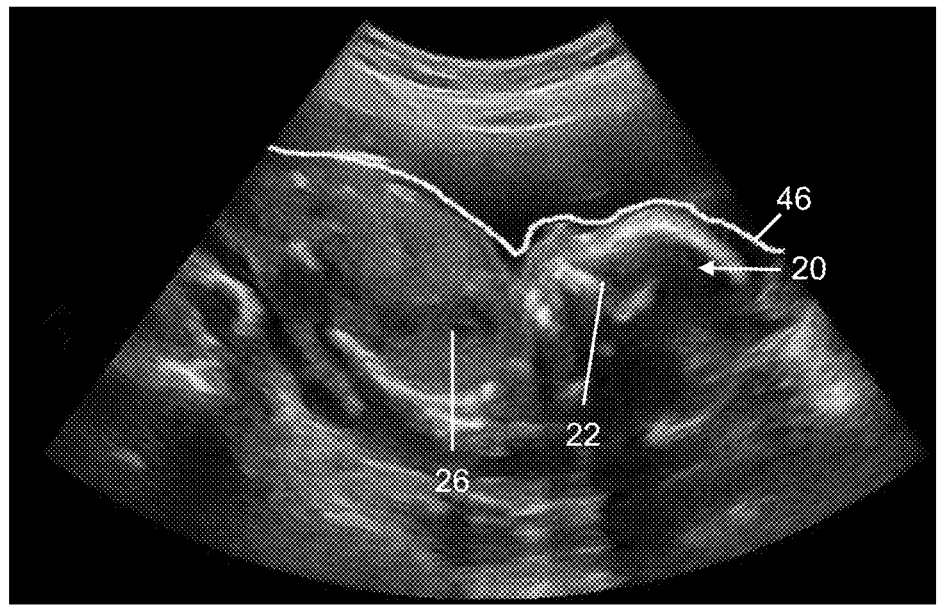
FIG. 3 is another fetal ultrasound image showing a cut line, according to an embodiment of the present invention.

Referring to FIG. 3, shown there is another example fetal ultrasound image with a different predicted cut line 46. In the ultrasound image of FIG. 3, profile of the fetus 20 contains only the fetal head 22 and a portion of the fetal abdomen 26. The profile of the fetus 20 does not have any protrusions for limbs. As a result, the cut line 46 in FIG. 3 may be a smoother less jagged line as compared to the cut line 40 of FIG. 2, while still closely following the profile of the fetus 20. Both cut lines 40 in FIG. 2 and cut line 46 of FIG. 3 may validly be used for removal of non-fetal data in the ultrasound frames before the generation of the 3D fetal representation.

In various embodiments, a cut line may generally be a freeform line, so that the cut line can freely adapt to the various contours of the profile of a fetus 20 visible in a given ultrasound image frame. However, in some embodiments, a cut line 40 may additionally or alternatively include a Bézier curve, a polynomial curve, a spline curve, a parametric curve, and/or a more complex curve made up of two or more of these types of curve. As discussed below, in some embodiments, the cut lines may be part of a shape for masking out the imaged non-fetal anatomy to be removed when generating the 3D fetal representation, or masking out the portion of the ultrasound image to be retained when generating the 3D fetal representation.

Referring back to FIG. 2, the image areas of the ultrasound frame that are on a distal side 42 of the predicted cut line 40, relative to the fetus 20, may be removed prior to generating the 3D fetal representation. The image areas of the ultrasound frame that are on a proximal side 44 of the predicted cut line 40, relative to the fetus 20, may then be used for the generation of the 3D fetal representation. By removing the portions of the ultrasound image on the distal side 42 of each ultrasound frame that compose the various slices forming the 3D fetal representation, portions of non-fetal anatomy will be excluded from the resulting 3D fetal representation. Alternately, in some embodiments, the portions of the ultrasound image on the distal side 42 of the ultrasound frame may simply be ignored when generating the 3D fetal representation.

As can be seen in the example of FIG. 2, the AI model may aim to predict the cut line 40 so that it is exterior to the imaged fetus 20, fetal head 22, and fetal abdomen 26, and so that it is exterior to (e.g., does not lie within) any imaged placenta, uterine wall 24, amniotic sac, umbilical cord, cervix and bladder. The predicted cut line 40 may, however, lie within the imaged amniotic fluid 32.

While amniotic fluid 32 generally has a dark appearance on an ultrasound image, simple edge detection techniques simply to trace the amniotic fluid may not accurately identify the profile of the fetus 20. This is because the presence of the amniotic fluid 32 may not be clear in all ultrasound images. For example, in some ultrasound images, some or all of the fetus 20 may be positioned adjacent to a wall of an amniotic sac such that there may not be an identifiable layer of amniotic fluid 32 appearing in the ultrasound image. Additionally or alternatively, in some ultrasound images, the umbilical cord may appear as being contiguous with the fetus 20 itself, such that an edge detection tracing technique may inadvertently include the umbilical cord and thus not identify a cut line 40 that accurately traces the profile of the fetus 20. In the present embodiments, by training an AI model to account for these different scenarios, the AI model is more likely to predict an accurate cut line 40 (e.g., a cut line that delineates the fetus 20 from the wall of the amniotic sac, and/or delineate the fetus 20 from the umbilical cord). Additional details related to the training of the AI model are discussed below.

As referenced above with respect to FIG. 3, some ultrasound images may be of a portion of the fetus rather than the whole fetus. For example, parts of the fetal anatomy that may be imaged in an ultrasound frame may include a face, a head, an ear, a nose, an eye, a neck, a torso, a foot, a leg, a hand, an arm, or a combination of any of these. An AI model may be trained similarly to predict the profile of the portion of the fetus 20 that appears in a given ultrasound image.

Figure 4:
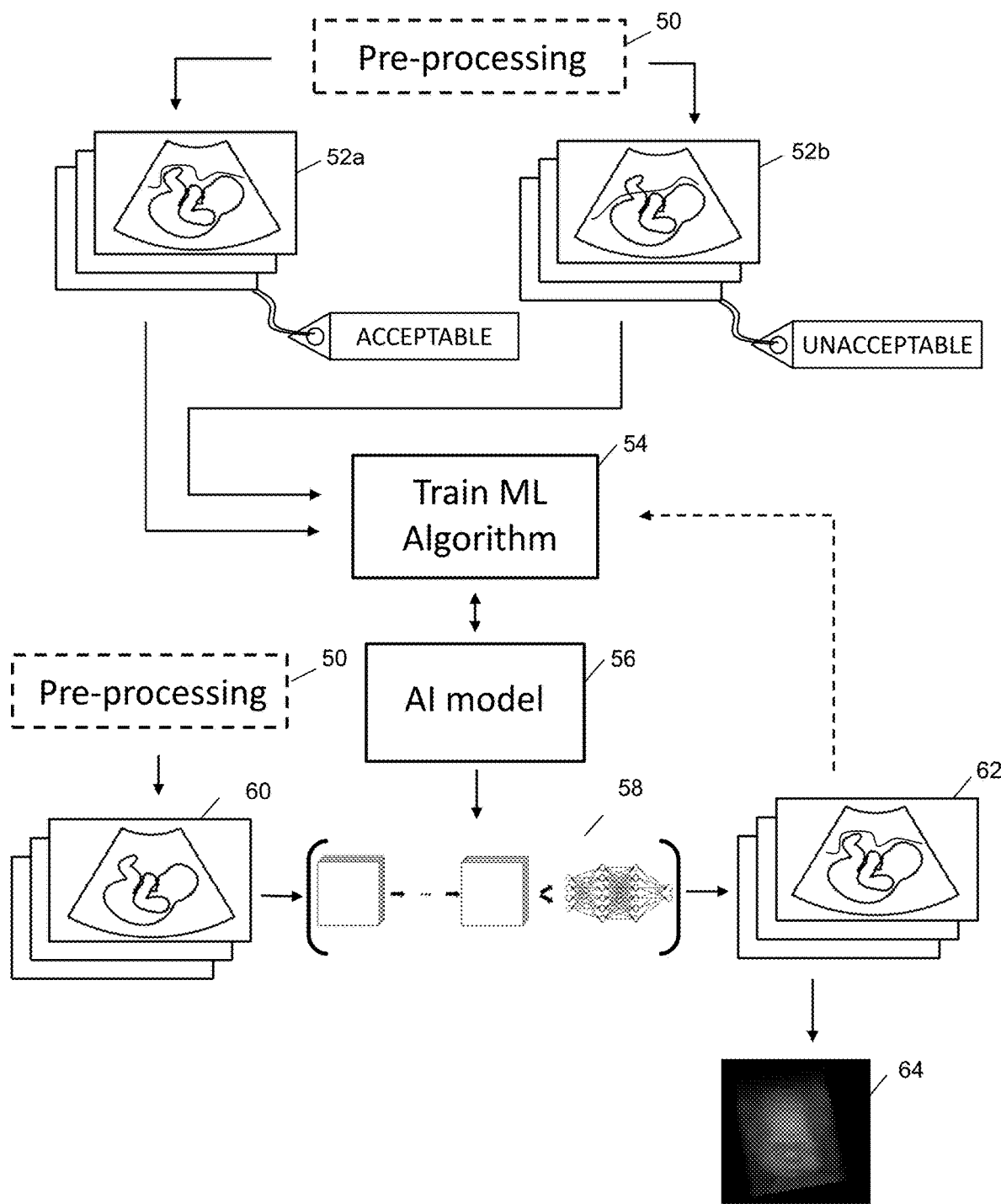
FIG. 4 is a schematic diagram of the training and deployment of an AI model, according to an embodiment of the present invention.

Referring to FIG. 4, shown there generally is a schematic diagram for training an AI model 56 to predict cut lines on fetal ultrasound image frames to generate a 3D fetal representation.

The AI model 56 may generally be trained by ultrasound frames that each have a labeled cut line that is positioned relative to an imaged fetus 20 in the training ultrasound frame. The training ultrasound frames may include ultrasound frames 52a with cut lines that are tagged as acceptable, and/or ultrasound frames 52b with cut lines that are tagged as unacceptable. Some of the labeled cut lines for training the AI model 56 may be defined using manual input. For example, a cut line on a training ultrasound frame may be labeled as acceptable if all points on the cut line are positioned exterior to the imaged fetus, and exterior to an imaged placenta, uterine wall, amniotic sac, umbilical cord, cervix, and bladder. In another example, a cut line on a training ultrasound frame may be labeled as acceptable if all points on the cut line are positioned within amniotic fluid imaged in the training ultrasound frame.

In contrast, a cut line on a training ultrasound frame may be labeled as unacceptable if any point on the cut line is positioned on or interior to the imaged fetus, or if any point on the cut line is positioned on or interior to an imaged placenta, uterine wall, amniotic sac, umbilical cord, cervix, or bladder.

In some embodiments, an optional pre-processing act 50 may be performed on the underlying ultrasound image frames 52a, 52b to facilitate improved performance and/or accuracy when training the machine learning (ML) algorithm. For example, since the desired output of the AI model is a cut line that generally traces the profile boundary of the fetus 20 (without needing to consider greyscale details within the various anatomy), it may be possible to pre-process the ultrasound images 52a, 52b through a high contrast filter to reduce the granularity of greyscale on the ultrasound images 52a, 52b.

Additionally or alternatively, since the desired cut line relative to the ultrasound images 52a, 52b should generally remain the same regardless of the scale of the ultrasound images, it may be possible to reduce scale of the ultrasound images 52a, 52b prior to providing the ultrasound images 52a, 52b to the training step 54. Reducing the scale of ultrasound images 52a, 52b as a preprocessing step may reduce the amount of image data to be processed during the training act 54, and thus may reduce the corresponding computing resources required for the training act 54 and/or improve the speed of the training act 54.

Various additional or alternative pre-processing acts may be performed in act 50. For example, these acts may include data normalization to ensure that the various ultrasound frames 52a, 52b used for training have generally the same dimensions and parameters.

Referring still to FIG. 4, the various training frames 52a, 52b may, at act 54, be used to train a ML algorithm. For example, the various training ultrasound frames 52a, 52b, may be inputted into a deep neural network that can learn how to predict a correct cut line on new ultrasound images. For example, the neural network may learn to detect the presence of the dark border (representative of the amniotic fluid 32) between the profile of a fetus 20 and any surrounding tissue so as to position the cutline within that dark border.

The result of the training may be the AI model 56, which represents the mathematical weights and/or parameters learned by the deep neural network to predict an accurate cut line on new fetal ultrasound images. The training act 54 may involve various additional acts (not shown) to generate a suitable AI model 56. For example, these various deep learning techniques such as regression, classification, feature extraction, and the like. Any generated AI models may be iteratively tested to ensure they are not overfitted and sufficiently generalized for identifying cut lines on new fetal ultrasound images. In various embodiments, the machine learning may be supervised or unsupervised.

For example, in some embodiments, once the training images are labelled, a deep neural network may use them as inputs and the associated expert cut-line as desired may be outputted to determine value sets of neural network parameters defining the neural networks.

As noted above, in some embodiments, the cut lines may be part of a shape that masks out the imaged non-fetal anatomy or the imaged fetus. For example, referring briefly simultaneously to FIG. 7B, the cut line 40b shown there is not simply a line, but rather as a closed shape that encompasses areas of the non-fetal anatomy above the cut line. Referring back to FIG. 4, in some embodiments, the neural network may be configured to receive one or more ultrasound images as input and to have a softmax layer as an output layer containing outputs which represent whether pixels of the corresponding input image fall within the area above the cut-line or not.

The training images file may include an image identifier field for storing a unique identifier for identifying an image included in the file, a segmentation mask field for storing an identifier for specifying the to-be-trimmed area, and an image data field for storing information representing the image.

In some embodiments, using a cross-validation method on the training process would optimize neural network hyper-parameters to try to ensure that the neural network can sufficiently learn the distribution of all possible fetus image types without overfitting to the training data. In some embodiments, after finalizing the neural network architecture, the neural network may be trained on all of the data available in the training image files.

In various embodiments, batch training may be used and each batch may consist of multiple images, thirty-two for example, wherein each example image may be gray-scale, 256*256 pixels, without any preprocessing applied to it.

In some embodiments, the deep neural network parameters may be optimized using the adam optimizer with hyper-parameters as suggested by Kingma, D. P., Ba, J. L.: Adam: a Method for Stochastic Optimization, International Conference on Learning Representations 2015 pp. 1-15 (2015), the entire contents of which are incorporated herewith. The weight of the convolutional layers may be initialized randomly from a zero-mean Gaussian distribution. In some embodiments, the Keras™ deep learning library with TensorFlow™ backend may be used to train and test the models.

In some embodiments, during training, many steps may be taken to stabilize learning and prevent the model from over-fitting. Using the regularization method, e.g., adding a penalty term to the loss function, has made it possible to prevent the coefficients or weights from getting too large. Another method to tackle the over-fitting problem is dropout. Dropout layers limit the co-adaptation of the feature extracting blocks by removing some random units from the neurons in the previous layer of the neural network based on the probability parameter of the dropout layer. Moreover, this approach forces the neurons to follow overall behaviour. This implies that removing the units would result in a change in the neural network architecture in each training step. In other words, a dropout layer performs similar to adding random noise to hidden layers of the model. A dropout layer with the dropout probability of 0.5 may be used after the pooling layers.

Data augmentation is another approach to prevent overfitting and add more transitional invariance to the model. Therefore, in some embodiments, the training images may be augmented on-the-fly while training. In every mini-batch, each sample may be translated horizontally and vertically, rotated and/or zoomed, for example.

Referring still to FIG. 4, after training has been completed, the sets of parameters stored in the storage memory may represent a trained neural network for masking out the imaged portions of the fetus.

In order to assess the performance of the model, the stored model parameter values can be retrieved any time to perform image assessment through applying an image to the neural networks represented thereby.

In some embodiments, the deep neural network may include various layers such as convolutional layers, max-pooling layers, and fully connected layers. In some embodiments, the final layers may include a softmax layer as an output layer having outputs which eventually would demonstrate respective determinations that an input set of pixels fall within a particular area above or below the cut-line. Accordingly, in some embodiments, the neural network may take at least one image as an input and output a binary mask indicating which pixels belong to the area above the cut-line (e.g., the AI model classifies which area each pixel belongs to).

To increase the robustness of the AI model 56, in some embodiments, a broad set of training data may be used at act 54. For example, ultrasound images at different gestational fetus ages can be included in the ultrasound images 52a, 52b used for training. For example, the training data may include ultrasound images for early obstetrics (OB) (up to 8 weeks), mid OB (between 8 and 26 weeks) and late OB (after 26 weeks). Cut lines may then be identified on the ultrasound images of these various fetus ages while training, so that the AI model 56 can learn to generate the cut line regardless of the age of the fetus.

Additionally or alternatively, the training act 54 in FIG. 4 may be repeated with different datasets for the different fetus ages to generate corresponding different AI models 56 that each generate cut lines for fetus age-specific ultrasound images. In this scenario, the appropriate AI model can be selected to be applied based on the age of the fetus. The age of the fetus can be determined in various ways: for example, based on patient examination information, OB measurements taken that correlate to age, and/or another AI model trained to identify fetus age of an imaged fetus.

In these example embodiments where the training datasets include fetuses of different ages, the resulting AI model(s) 56 may be more robust. This is because later-stage fetuses may have grown to a stage where it is not easy to delineate between the profile of the fetus 20 and the surrounding tissue (e.g., the usually dark appearance of the amniotic fluid 32 may not be as apparent on the ultrasound images). By having the dataset include these scenarios, the AI model 56 (if only a single AI model 56 is generated) may learn to recognize these situations so as to produce accurate cut lines when scanning fetuses that are in later pregnancy stages. Or, if the different fetus-age datasets are used to generate different corresponding AI models 56, then the potentially more challenging cut lines to predict for ultrasound images of late OB fetuses can be avoided when training the earlier-stage fetus images. This may make the AI models 56 for the earlier-stage fetuses easier to train, so that they are more likely to converge on an accurate AI model 56 for ultrasound images of early OB and mid OB fetuses. The early OB and mid OB AI models my then be more confidently used with early OB and mid OB stage fetuses.

Referring still to FIG. 4, once a satisfactory AI model 56 is generated, the AI model 56 may be deployed for execution on a neural network 58 to predict cut lines on new fetal ultrasound images 60. Notably, the neural network 58 is shown in FIG. 4 for illustration as a convolution neural network—with various nodes in the input layer, hidden layers, and output layers. However, in various embodiments, different arrangements of the neural network 58 may be possible.

In various embodiments, prior to being processed for prediction of cut lines thereon, the new ultrasound images 60 may optionally be pre-processed. This is shown in FIG. 4 with the pre-processing act 50 in dotted outline. In some embodiments, these pre-processing acts 50 may be analogous to the pre-processing acts 50 performed on the training ultrasound frames 52*a*, 52*b* (e.g., processing through a high contrast filter and/or scaling), to facilitate improve accuracy in generating a predicted cut line.

In various embodiments, the new fetal ultrasound images 60 may be live images acquired by an ultrasound imaging system (e.g., the system discussed with respect to FIG. 10 below). For example, the AI model 56 may be deployed for execution on the scanner 131 and/or the display device 150 discussed in more detail below. Additionally or alternatively, the AI model 56 may be executed on stored images 60 that were previously acquired (e.g., as may be stored on a Picturing Archiving and Communication System (PACS)). When executed in this manner, the AI model 56 may allow the neural network 58 to predict cut lines on the new ultrasound frames 60, resulting in a series of ultrasound frames 62 with predicted cut lines defined thereon. The ultrasound frames 62 with predicted cut lines may then be used for the generation of a 3D representation 64 of the fetus. As shown in FIG. 4 for illustrative purposes, the 3D representation 64 is a 3D surface of the face of the fetus 20. However, in various embodiments, additional anatomical features of the fetus 20 may also be shown in the 3D representation 64.

In some embodiments, the ultrasound frames 62 with predicted cut lines may optionally each be labeled as either acceptable or unacceptable, and these labeled ultrasound frames may themselves be used for training and/or reinforcing the AI model 56. For example, the frames shown in FIGS. 2 and 3 may be used for training and/or reinforcing the AI model 56. This is shown in FIG. 4 with a dotted line from the ultrasound frames 62 with the predicted cut lines being provided to the training act 54.

Figure 5:
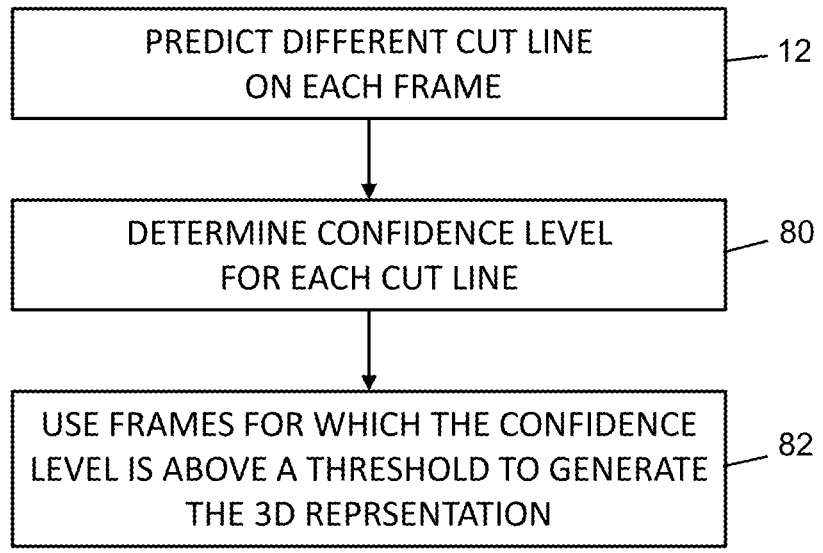
FIG. 5 is a flowchart for selecting ultrasound frames for the generation of the 3D representation, according to an embodiment of the present invention.

Referring to FIG. 5, a method for selecting ultrasound frames for the generation of a 3D fetal representation is shown. The first step 12 may correspond to the second step in FIG. 1, in which a different cut line is predicted on each of the acquired fetal ultrasound frames, where possible. As part of the process for generating the 3D fetal representation, after a cut line has been predicted, the AI model 56 may determine a confidence level for the prediction of each cut line, in step 80. For example, the confidence level may be rated high (e.g. above 70%) if the AI model 56 deems that there is a generally low level of uncertainty in the possible positioning of the predicted cut line. In contrast, the confidence level may be rated low (e.g. 50% or below) if the AI model 56 deems that there is a relatively higher level of uncertainty in the possible positioning of the predicted cut line. Higher levels of uncertainty may arise, for example, for ultrasound frames in which two adjacent body parts have the same or a similar image density on the ultrasound frame.

In step 82, the ultrasound frames for which the confidence level is above a threshold may then be used to generate the 3D fetal representation, with the other ultrasound frames for which the confidence level is below the threshold being discarded or ignored.

For example, the process may include removing, from each of the ultrasound frames for which the confidence level is above the threshold, ultrasound data on a distal side of the cut line relative to the image of the fetus appearing on the ultrasound frame. The remaining ultrasound data in each of the ultrasound frames from which ultrasound data has been removed may then be used to generate the 3D fetal representation.

By using only the ultrasound frames with cut lines for which the confidence level is above the threshold, the calculations required for generating the 3D fetal representation may more likely be accurate. For example, the resultant 3D fetal representation may less likely include non-fetal anatomy and/or cut off portions of the fetal anatomy than if the full set of ultrasound frames were used. Since frames for which the predicted cut line is below the confidence threshold may be dropped, it is possible that there may be gaps in the various slices that form the 3D fetal representation. To reduce the potential appearance of jaggedness, interpolation and/or smoothing algorithms may be used when generating the 3D fetal representation.

In some embodiments, instead of discarding or ignoring the ultrasound frames for which the confidence is below the threshold, the predicted cut line for a nearby frame may be used for these ultrasound frames. For example, it may be the case that the confidence level for the cut line predicted for an adjacent frame (e.g., a frame acquired immediately before or after) or a neighboring frame (e.g., a frame acquired with a certain number of frames) is above the acceptance threshold, then the cut line predicted on that adjacent or neighboring frame can be used on the ultrasound frame for which the predicted cut line has not met the confidence threshold. Such a configuration may allow more ultrasound frames to be included in the slices that form the 3D fetal representation and reduce the possibility of the generated 3D fetal representation appearing jagged (as may be the case if too many ultrasound frames are discarded or ignored when generating the 3D fetal representation).

Figure 6:
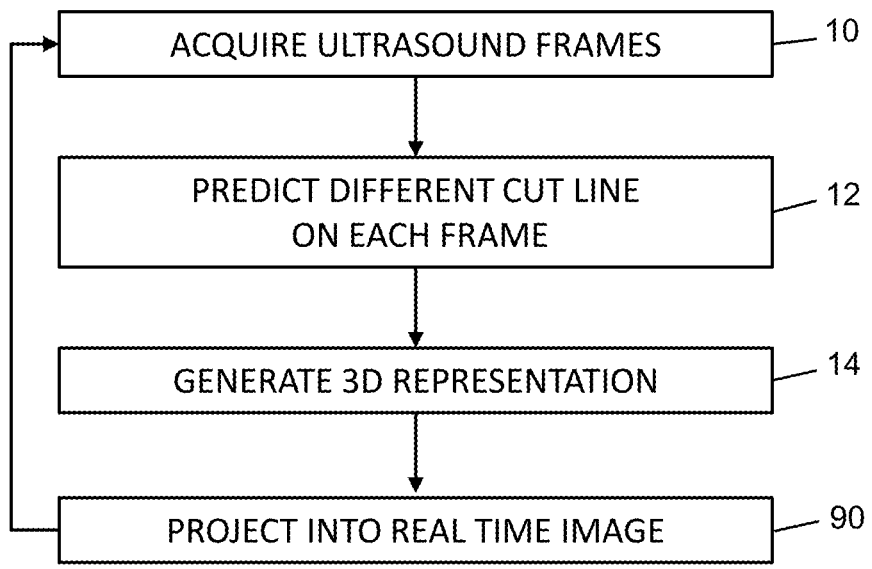
FIG. 6 is a flowchart for generating a 4D ultrasound representation, according to an embodiment of the present invention.

Referring to FIG. 6, a method is shown for generating a 4D fetal ultrasound representation, which may be a 3D representation that varies in real time as the fetus moves. The first three steps 10, 12, 14 may be the same as those in FIG. 1, in which a number of ultrasound frames are acquired, cut lines are predicted and a 3D fetal representation is generated. In step 90, the generated 3D fetal representation may then be projected into a real time image that is displayed. The process then reverts to step 10 to repeat the cycle. Every time the cycle is repeated, the real time image may be updated with the most recent 3D fetal representation that is generated.

As noted above, in some embodiments, a motor in the head of the scanner may tilt the ultrasonic transducer to acquire ultrasound frames at different angles. In various embodiments, the motor may perform a sweep of the possible angles of acquisition at a frame rate of 15-40 frames per second (fps). These frames can be included in the slices forming the 3D fetal representations, so that resultant 4D fetal representations can have a volume rate of 1-3 volumes per second (vps). In various embodiments, the 4D fetal frame rate can vary depending on the number of slices included in each 3D fetal representation. For example, if fewer individual ultrasound frames are included as slices when generating the 3D fetal representation, the 4D volume rate may be improved (though each individual frame may not have as much resolution). Conversely, if increased resolution in the 3D fetal representation is desired, a higher number of individual ultrasound frames may be included as slices when generating each 3D fetal representation, and the corresponding 4D volume rate may be decreased.

Figure 7A:
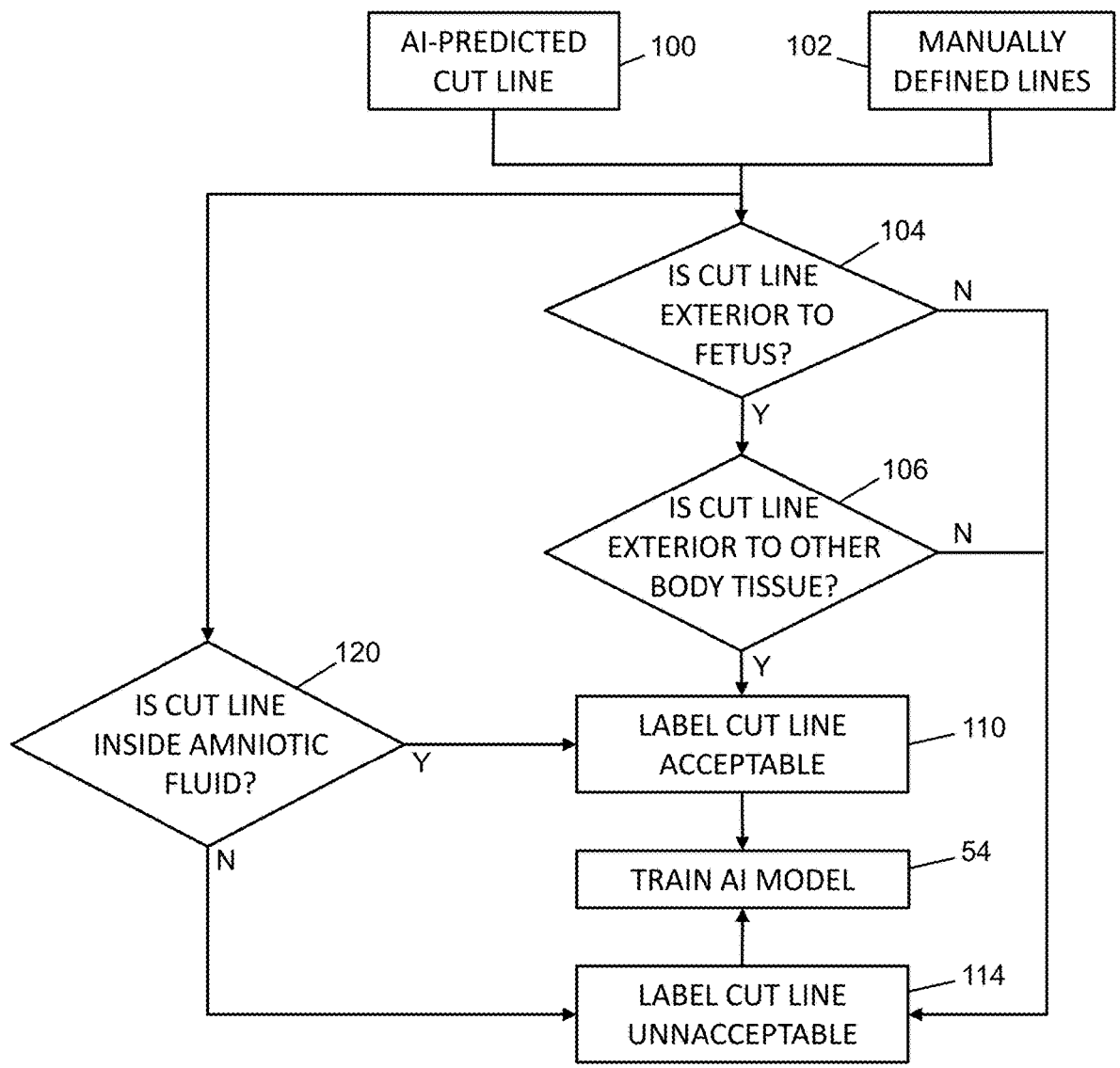
FIG. 7A is a flowchart for training an AI model, according to an embodiment of the present invention.

Referring to FIG. 7A, a flowchart for training the AI model 50 is shown, according to an example embodiment. For example, the acts of FIG. 7A may be performed as part of steps to train the ML algorithm (e.g., as part of act 54 of FIG. 4), where ultrasound frames with manually-defined cut lines 52*a*, 52*b* and/or ultrasound frames with AI-predicted cut lines 62 can be provided to train the AI model.

In FIG. 7A, ultrasound frames with AI-predicted cut lines may be provided in step 100 and ultrasound frames with manually defined cut lines may be provided in step 102. In step 104, for each ultrasound frame provided, a determination may be made as to whether the cut line is exterior to the imaged fetus 20 (e.g., as shown in FIG. 2). If the cut line is exterior to the imaged fetus 20, then, in step 106, it may be determined whether the cut line is exterior to other body tissue, e.g., body tissue of the mother that is imaged on the ultrasound frame. If the cut line is exterior to the other body tissue, then, in step 110, the ultrasound image with the cut line may be labeled as acceptable. The ultrasound image with the acceptable cut line may then be used to train the AI model in step 54 of FIG. 4.

Returning to step 104, if the cut line is not exterior to the imaged fetus, then the cut line is not acceptable, and the corresponding ultrasound frame with the cut line may be labeled as unacceptable in step 114. The ultrasound image with the unacceptable cut line may then be used to train the AI model at step 54.

Returning to step 106, if the cut line is not exterior to other imaged body tissue, then the cut line is not acceptable, and the corresponding ultrasound frame with the cut line may be labeled as unacceptable in step 114. The ultrasound image with the unacceptable cut line may then be used to train the AI model 50 in step 54 of FIG. 4.

Referring still to FIG. 7A, an additional or alternative possibility to analyze the ultrasound frames with AI-predicted cut lines provided in step 100 and ultrasound frames with manually defined cut lines in step 102 is shown in step 120. In step 120, it is determined whether the cut line lies within the imaged amniotic fluid 32 (e.g., as shown in FIG. 2). If the cut line lies within the amniotic fluid 32, then the ultrasound frame with the cut line may be labeled as acceptable in step 110. The ultrasound image with the acceptable cut line may then be used to train the AI model 50 in step 54.

If, in step 120, the cut line does not lie within the amniotic fluid, then the ultrasound frame with the cut line may be labeled as unacceptable in step 114. The ultrasound image with the unacceptable cut line may then be used to train the AI model 50 in step 54 of FIG. 4.

It can therefore be seen that there are a variety of different ways in which an ultrasound frame may be analyzed. Other ways may be possible in other embodiments. For example, while FIG. 7A shows step 120 being an alternative path to steps 104 and 106 for determining cut line acceptability, in various embodiments, the step 120 may be may performed in addition to the determinations made at steps 104 and 106.

As discussed above in relation to FIG. 1, to increase the robustness of the AI model, the ultrasound frames used for training may include various views of a prenatal fetus. In various embodiments, the acquisition protocol for acquiring the training ultrasound frames may first specify that the ultrasound operator is to acquire a frontal midsagittal view of the fetus 20 (e.g., as is shown in FIG. 2). Once this view has been acquired, the acquisition protocol may then indicate that additional frames are to be acquired as the probe is rotated at a number of increments until a transverse view of the fetus is acquired, and then continuing with additional rotational increments until the probe has returned to a frontal midsagittal view of the fetus. In an example, the increments may be 45 degrees, 90 degrees (e.g., a transverse view), then 135 degrees, then 180 degrees; so that a total of 4 different planes are acquired. The ultrasound frames from these various views can then be used to identify cut lines, for training the AI model as discussed herein.

In some embodiments, this rotational protocol may also be performed not just from a frontal midsagittal view of the fetus, but also from one or more of: a rear midsagittal view of the fetus (e.g., when the probe head is facing the backside of the fetus 20), a left coronal view of the fetus 20 (e.g., when the probe head is facing the left side of the fetus 20), a right coronal view of the fetus 20 (when the probe head is facing the right side of the fetus 20), a superior coronal view of the fetus 20 (when the probe head is facing the head of the fetus 20), and a posterior coronal view of the fetus 20 (when the probe head is facing the feet of the fetus 20). Cut lines can be identified on these various views of the fetus for training the AI model 56, so that the AI model 56 may be able to predict cut lines when corresponding views of the fetus are obtained on newly acquired ultrasound images 60.

Unskilled or novice ultrasound operators may not have developed the skill to obtain a traditional midsagittal view of the fetus 20 that provides an accurate profile of the fetus 20. Thus, training the AI model 56 with such off-angle ultrasound images may increase the robustness of the AI model 56, so as to be operational when fetal ultrasound images are acquired by unskilled or novice operators.

Figure 7B:
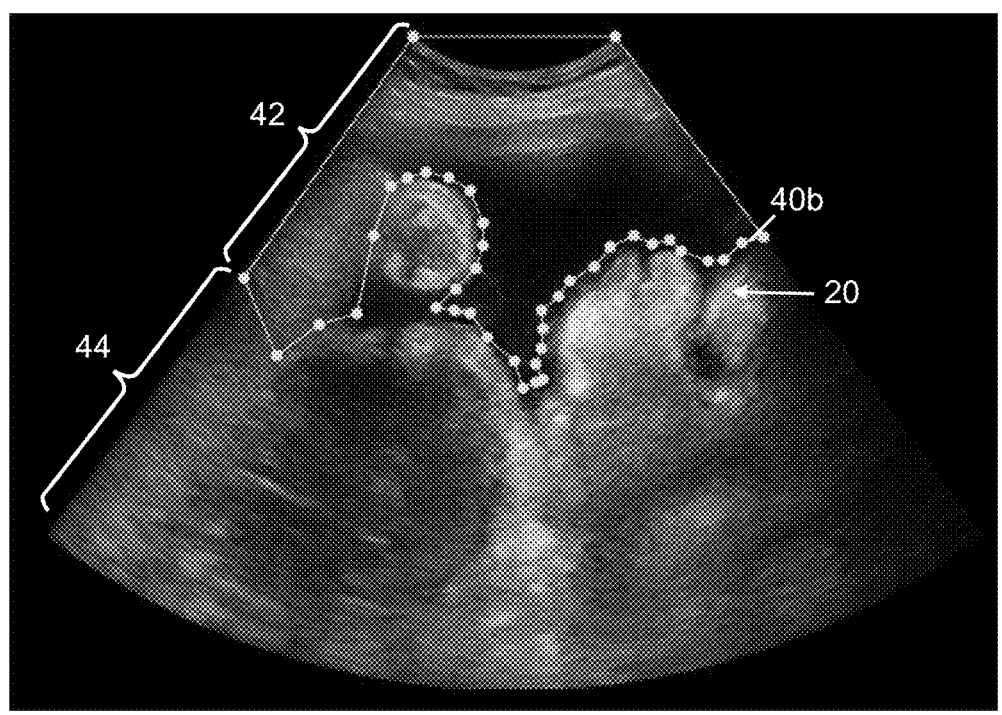
FIG. 7B is another fetal ultrasound image showing a cut line, according to an embodiment of the present invention.

For example, referring to FIG. 7B, shown there is another example fetal ultrasound image with a cut line, according to an embodiment of the present invention. In FIG. 7B, the image acquired of the fetus 20 is rotationally off angle from a midsagittal view that would generally provide a better view of the profile of the fetus 20. An example cut line 40b is shown that delineates between anatomy of the fetus 20 below the cut line 40b and non-fetal anatomy above the cut line 40b that is not to be included when generating the 3D fetal representation. Similar to the ultrasound image shown in FIG. 2, the image areas of the ultrasound frame that are on a distal side 42 of the cut line 40b, relative to the fetus 20, may be removed prior to generating the 3D fetal representation. The image areas of the ultrasound frame that are on a proximal side 44 of the cut line 40b, relative to the fetus 20, may then be used for the generation of the 3D fetal representation.

In various embodiments, these different views from the acquisition protocol may all be obtained for fetuses at the different gestational ages discussed above. As noted, the ability to identify a cut line may be easier for early OB and mid OB fetuses, than for late OB fetuses. Thus, obtaining these various views for fetuses of the various gestational ages discussed above can increase the performance of the trained AI model 56, so that predicted cut lines will more likely be accurate. As noted above, in FIG. 7B, the cut line 40b is shown as part of a shape that masks out the non-fetal anatomy to be removed prior to generating the 3D fetal representation.

By training the AI model 56 to predict cut lines on a wide variety of views of the fetus, the present embodiments can reduce the time and skill needed by an operator to obtain a 3D fetal representation. In traditional methods of generating a 3D fetal representation, an ultrasound operator typically first identifies a view of the fetus 20 as close to the midsagittal view as possible (which takes time to position the ultrasound probe). Once this view is found, the operator may position a Region Of Interest (ROI) for placement of the fixed cut line for generating the 3D fetal representation. Since it is generally desired to get a 3D view of the face of the fetus 20, and since the position of the probe is often not directly over the center of the front view of the fetus 20, the operator typically rotates the 3D fetal representation after it is generated so that the complete frontal view of the fetus can be viewable. These various steps in a traditional method of generating a 3D fetal representation are lengthy and cumbersome.

In contrast, in the present embodiments, since the AI model 56 is trained to detect cut lines on a wide variety of views of the fetus, the AI model 56 can immediately be applied when at least a portion of the fetus is scanned by the ultrasound probe—without the operator having to first identify the frontal midsagittal view of the fetus. In this manner, when the probe being placed in an arbitrary orientation with respect to the fetus 20, a 3D fetal representation of that portion of the anatomy can generally be generated and visualized—regardless of whether it is a frontal, rear, side, superior, or posterior view of the fetus 20, or any blend of these views.

Moreover, since the AI model 56 can work to immediately apply a cut line in real-time, it is possible to generate a 3D representation of the fetus as the probe moves over the surface of the skin. In this manner, the resultant generated 3D fetus representation may provide visualization that works similar to what may be expected if a flashlight was able to "see" through the surface of the skin. E.g., the 3D representation of the fetus may be in line with the center of the probe head, so as to give an operator a live 3D representation of the fetus that is in the direct field of view of the center of the ultrasound probe.

Such a "flashlight" mode of operation may be different from the traditional methods of generating a 3D representation of the fetus noted above, where during the various steps required to generate the 3D fetal representation, the fetus may move or the generated 3D fetal representation may need to be rotated to permit viewing of the face, such that the generated 3D visualization may not align with the center of the probe. Having the generated 3D visualization correspond with the center of the probe in real-time as the probe is being moved may be desirable in various situations. For example, such a mode of operation may be desirable for the operator to more accurately identify the position of the face in a real-time during delivery of a baby, since the fetus should generally be facing up during delivery and not facing down.

In various embodiments, when visualizing the 3D fetal representation, different ultrasound modes to highlight different anatomy may be used. For example, in some embodiments, it may be possible to image in a skeleton mode that highlights the bone structure of the fetus 20. This would allow the bone structure to be visible in the generated 3D fetal representation. Such a skeleton mode may be different from a regular skin realistic mode for visualizing the 3D fetal representation.

In the embodiments discussed above, the 3D fetal representation is generally a 3D surface that follows the different cut lines predicted by the AI model 56 for the various slices formed from the underlying 2D ultrasound images. However, in some embodiments, it may be possible to generate a full 3D volumetric representation of the fetus 20 that provides not just a 3D surface showing the side of the fetus proximate to the transducer head. For example, this may be performed if multiple cut lines are included when training the AI model 56, so that the AI model 56 can predict multiple cut lines on new ultrasound images 60.

Figure 8:
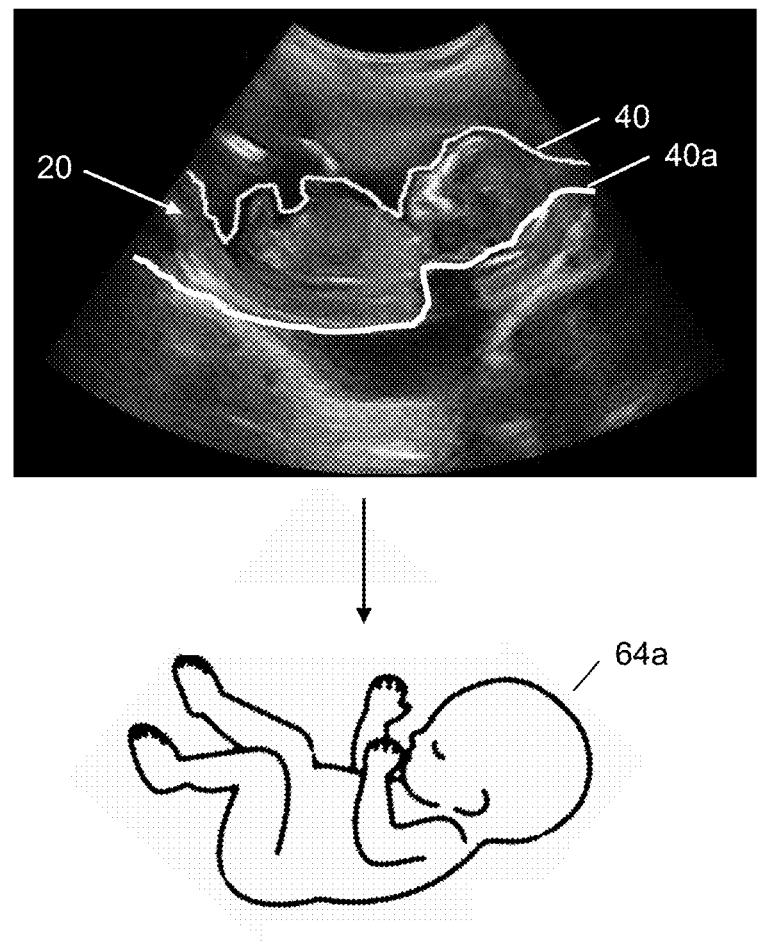
FIG. 8 is a flowchart illustrating a fetal ultrasound image with more than one predicted cut line and resulting generation of a predicted 3D fetal representation, according to an embodiment of the present invention.

Referring to FIG. 8 shown there generally is a flowchart of a fetal ultrasound image with more than one predicted cut line, and resulting generation of a predicted 3D fetal volume. The fetal ultrasound image shown in FIG. 8 is the same as that shown in FIG. 2, except in addition to the cut line 40 shown in FIG. 2, the ultrasound image is shown with a second cut line 40a. This second cut line 40a may delineate the fetus 20 from the non-fetal anatomy on the distal side of the fetus 20 relative to the probe head. In various embodiments, the training data (e.g., as discussed above with respect to FIG. 4) may include inserting such an additional cut line 40a, so that the two cut lines together 40, 40a, delineate the fetus 20 from non-fetal anatomy on both the proximate and distal sides of the fetus 20 relative to the probe head. The AI model 56 may correspondingly be trained to identify the multiple cut lines 40, 40a on new fetal ultrasound images.

When multiple cut lines 40, 40a are identified by the AI model 56 on each ultrasound frame, this may allow only the imaged fetus 20 between the cut lines 40, 40a to be retained when generating the 3D fetal representation. When this fetal ultrasound information is used as slices across various ultrasound image frames, the generated 3D fetal representation may be a 3D fetal volume 64a that shows the 3D contours of the fetus 20 both on the proximate side of the fetus 20 relative to the probe head, and also on the distal side of the fetus 20 relative to the probe head. In the example of FIG. 8, the proximate side of the fetus 20 relative to the probe head is the front side of the fetus 20, but in various embodiments, the proximate side of the fetus 20 relative to the probe head may be the back side of the fetus 20 or any other perspective view of the fetus. As discussed above, the training ultrasound image frames may include various views of the fetus 20, and multiple cut lines may be defined on these various views (e.g., for training or prediction by the AI model 56).

Having generated the 3D fetal volume, in some embodiments, the 3D fetal volume may be manipulated during visualization (e.g., rotated along various axis) so that different aspects of the fetus 20 can be seen on a display device. In this manner, the visualization of the 3D fetal volume may be different from the "flashlight" mode discussed above, because the view of the 3D fetal volume may not necessarily line up with the center of the probe.

Figure 9:
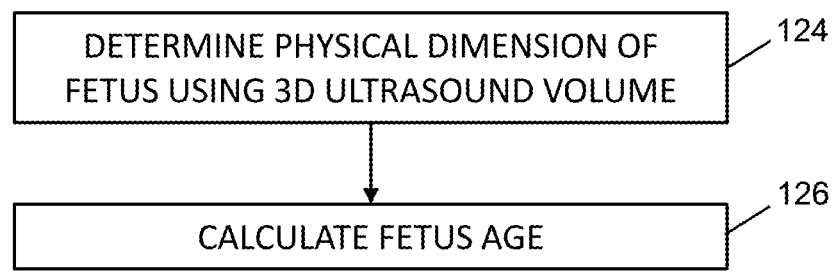
FIG. 9 is a flowchart for calculating the age of a fetus, according to an embodiment of the present invention.

Referring to FIG. 9, a flowchart is shown for calculating the age of a fetus. From the 3D fetal ultrasound volume, a physical dimension of the fetus may be determined, in step 124. For example, these dimensions may correspond to standard OB measurements that may otherwise require specific 2D OB ultrasound views to be acquired by an operator. In various embodiments, the physical dimensions that is determined may be the crown rump length (CRL), biparietal diameter (BPD), head circumference (HC), abdominal circumference (AC), femur length (FL), cephalic index (CI), humerus length (HL), binocular distance (BOD), and/or intraocular diameter (IOD). More than one physical dimension may be determined from the 3D fetal ultrasound volume. In this manner, the standard OB exam may be simplified as the operator may not need to spend time to acquire the various standard views to obtain these various measurements. Instead, these measurements may be obtained by simply acquiring frames that allow the generation of a 3D fetal volume as discussed herein.

In some embodiments, after a physical dimension of the fetus has been determined, an age of the fetus may be calculated using the physical dimension (step 126) since in general, there is a correspondence between the age of a fetus and its physical dimensions. Determination of the age of the fetus may therefore be performed by the present system without human input to measure the physical dimension.

Figure 10:
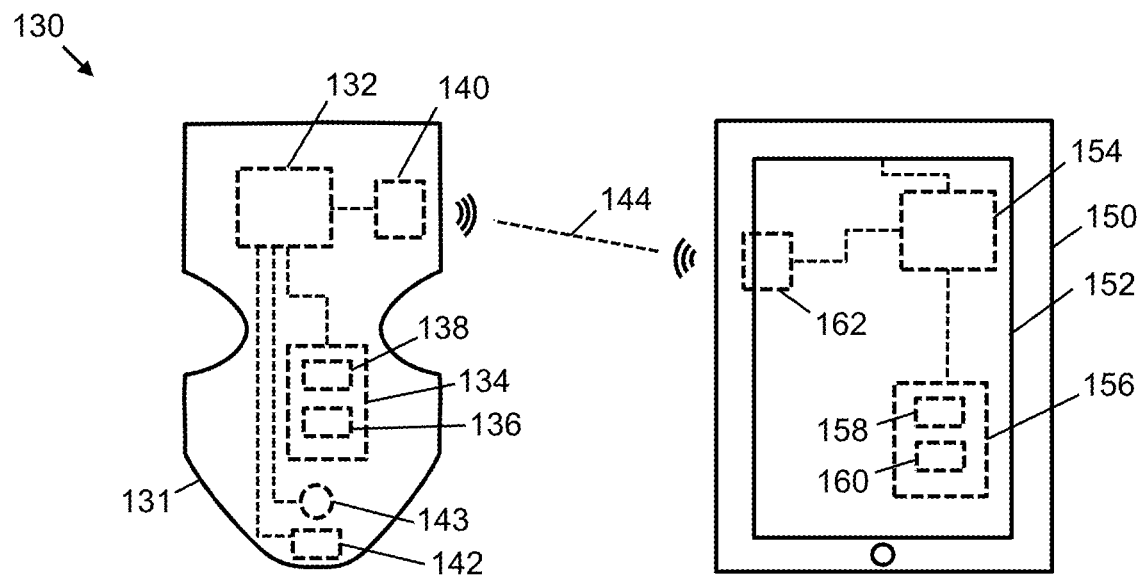
FIG. 10 is a schematic diagram of an ultrasound imaging system, according to an embodiment of the present invention.

Referring to FIG. 10, an exemplary system 130 is shown for generating a 3D fetal representation. The system 130 includes an ultrasound scanner 131 with a processor 132, which is connected to a non-transitory computer readable memory 134 storing computer readable instructions 136, which, when executed by the processor 132, may cause the scanner 131 to provide one or more of the functions of the system 130. Such functions may be, for example, the acquisition of ultrasound data, the processing of ultrasound data, the scan conversion of ultrasound data, the transmission of ultrasound data or ultrasound frames to a display device 150, the detection of operator inputs to the ultrasound scanner 131, and/or the switching of the settings of the ultrasound scanner 131.

Also stored in the computer readable memory 134 may be computer readable data 138, which may be used by the processor 132 in conjunction with the computer readable instructions 136 to provide the functions of the system 130. Computer readable data 138 may include, for example, configuration settings for the scanner 131, such as presets that instruct the processor 132 how to collect and process the ultrasound data for a given body part (e.g., skeleton mode), and how to acquire a series of ultrasound frames for the generation of a 3D fetal representation.

The scanner 131 may include an ultrasonic transducer 142 and a motor 143 that tilts the ultrasonic transducer 142 relative to the body of the scanner 131 in order to acquire ultrasound frames at a range of angles while the scanner 131 is held steady by an operator.

The scanner 131 may include a communications module 140 connected to the processor 132. In the illustrated example, the communications module 140 may wirelessly transmit signals to and receive signals from the display device 150 along wireless communication link 144. The protocol used for communications between the scanner 131 and the display device 150 may be WiFi™ or Bluetooth™, for example, or any other suitable two-way radio communications protocol. In some embodiments, the scanner 131 may operate as a WiFi™ hotspot, for example. Communication link 144 may use any suitable wireless communications network connection. In some embodiments, the communication link between the scanner 131 and the display device 150 may be wired. For example, the scanner 131 may be attached to a cord that may be pluggable into a physical port of the display device 150.

In various embodiments, the display device 150 may be, for example, a laptop computer, a tablet computer, a desktop computer, a smart phone, a smart watch, spectacles with a built-in display, a television, a bespoke display or any other display device that is capable of being communicably connected to the scanner 131. The display device 150 may host a screen 152 and may include a processor 154, which may be connected to a non-transitory computer readable memory 156 storing computer readable instructions 158, which, when executed by the processor 154, cause the display device 150 to provide one or more of the functions of the system 130. Such functions may be, for example, the receiving of ultrasound data that may or may not be pre-processed; scan conversion of received ultrasound data into an ultrasound image; processing of ultrasound data in image data frames; the display of a user interface; the control of the scanner 131; the display of an ultrasound image on the screen 152; the prediction of cut lines on ultrasound frames; the generation of 3D fetal representations using ultrasound frames with cut lines; the generation of 4D fetal representations; and/or the storage, application, reinforcing and/or training of an AI model 56 that predicts cut lines on ultrasound frames.

Also stored in the computer readable memory 156 may be computer readable data 160, which may be used by the processor 154 in conjunction with the computer readable instructions 158 to provide the functions of the system 130. Computer readable data 160 may include, for example, settings for the scanner 131, such as presets for acquiring ultrasound data; settings for a user interface displayed on the screen 152; and/or data for one or more AI models 56 for predicting cut lines in fetal ultrasound frames. Settings may also include any other data that is specific to the way that the scanner 131 operates or that the display device 150 operates.

It can therefore be understood that the computer readable instructions and data used for controlling the system 130 may be located either in the computer readable memory 134 of the scanner 131, the computer readable memory 156 of the display device 150, and/or both the computer readable memories 134, 156.

The display device 150 may also include a communications module 162 connected to the processor 154 for facilitating communication with the scanner 131. In the illustrated example, the communications module 162 wirelessly transmits signals to and receives signals from the scanner 131 on wireless communication link 144. However, as noted, in some embodiments, the connection between scanner 131 and display device 150 may be wired.

Figure 11:
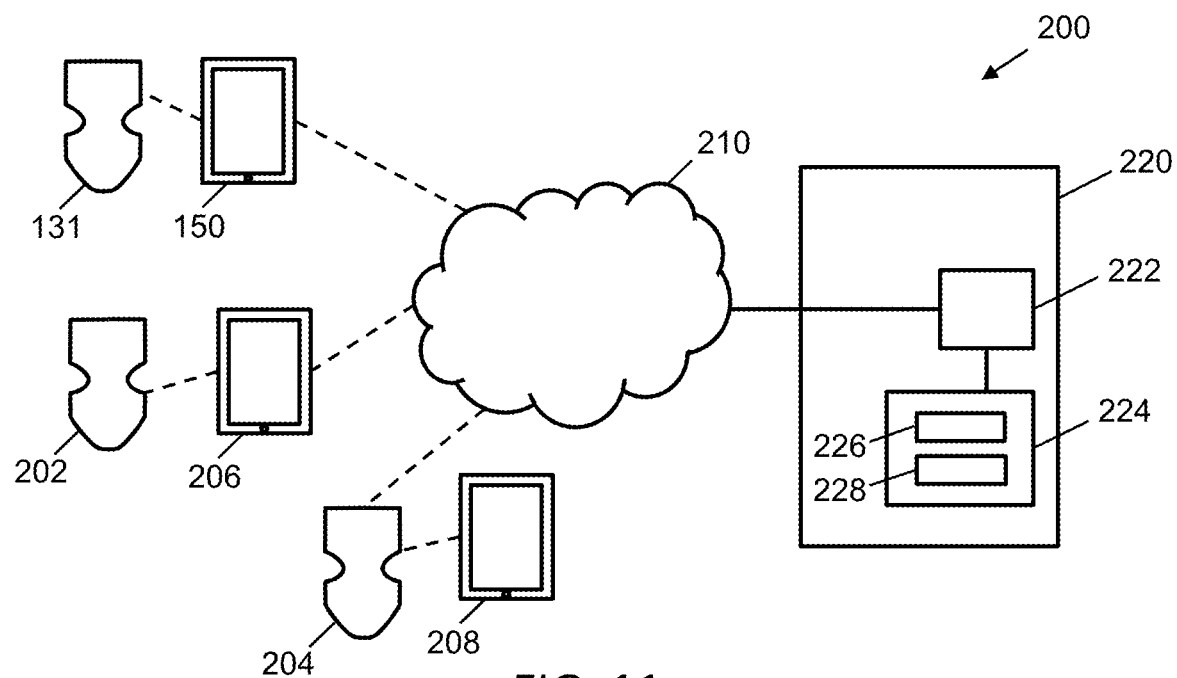
FIG. 11 is a schematic diagram of a system with multiple ultrasound scanners, according to an embodiment of the present invention.

Referring to FIG. 11, a system 200 is shown in which there are multiple similar or different scanners 131, 202, 204 connected to their corresponding display devices 150, 206, 208 and either connected directly, or indirectly via the display devices, to a communications network 210, such as the internet. The scanners 131, 202, 204 may be connected onwards via the communications network 210 to a server 220.

The server 220 may include a processor 222, which may be connected to a non-transitory computer readable memory 224 storing computer readable instructions 226, which, when executed by the processor 222, cause the server 220 to provide one or more of the functions of the system 200. Such functions may be, for example, the receiving of fetal ultrasound frames, the processing of ultrasound data in ultrasound frames, the control of the scanners 131, 202, 204, the prediction of cut lines on ultrasound frames, and/or machine learning activities related to one or more AI models 56 (as discussed above in relation to FIG. 4). Such machine learning activities may include the training and/or reinforcing of one or more AI models 56 for predicting cut lines in fetal ultrasound frames.

Also stored in the computer readable memory 224 may be computer readable data 228, which may be used by the processor 222 in conjunction with the computer readable instructions 226 to provide the functions of the system 200. Computer readable data 228 may include, for example, settings for the scanners 131, 202, 204 such as preset parameters for acquiring ultrasound data, settings for user interfaces displayed on the display devices 150, 206, 208, and data for one or more AI models 56. For example, the AI model 50 may be used to predict cut lines on fetal ultrasound frames, as discussed above. Settings may also include any other data that is specific to the way that the scanners 131, 202, 204 operate or that the display devices 150, 206, 208 operate.

It can therefore be understood that the computer readable instructions and data used for controlling the system 200 may be located either in the computer readable memory of the scanners 131, 202, 204, the computer readable memory of the display devices 150, 206, 208, the computer readable memory 224 of the server 220, or any combination of the foregoing locations.

As noted above, even though the scanners 131, 202, 204 may be different, each fetal ultrasound frame acquired may be used by the AI model 56 for training. Likewise, the fetal ultrasound frames acquired by the individual scanners 131, 202, 204 may all be processed against the AI model 56 for prediction of the cut lines and/or for reinforcement of the AI model 56.

In some embodiments, the AI models 56 present in the display devices 150, 206, 208 may be updated from time to time from an AI model 56 present in the server 220, where the AI model present in the server is continually trained using ultrasound frames with cut lines acquired by multiple scanners 131, 202, 204.

Embodiments of the invention may be implemented using specifically designed hardware, configurable hardware, programmable data processors configured by the provision of software (which may optionally include 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, main computers, computer workstations, and the like. For example, one or more data processors in a control circuit for a device may implement methods as described herein by executing software instructions in a program memory accessible to the processors.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

The embodiments may also be provided in the form of a program product. The program product may include any non-transitory medium which carries a set of computer-readable instructions which, when executed by a data processor, cause the data processor to execute a method of the invention. Program products according to the invention may be in any of a wide variety of forms. The program product may include, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

Where a component (e.g. software, processor, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments. In some embodiments, the components of the systems and apparatuses may be integrated or separated. Moreover, the operations of the systems and apparatuses disclosed herein may be performed by more, fewer, or other components and the methods described may include more, fewer, or other steps. In other instances, well known elements have not been shown or described in detail and repetitions of steps and features have been omitted to avoid unnecessarily obscuring the invention. Screen shots may show more or less than the examples given herein. Accordingly, the specification is to be regarded in an illustrative, rather than a restrictive, sense.

It is therefore intended that the appended claims and claims hereafter introduced are interpreted to include all such modifications, permutations, additions, omissions and subcombinations as may reasonably be inferred. The scope of the claims should not be limited by the embodiments set forth in the examples but should be given the broadest interpretation consistent with the description as a whole.

C. Interpretation of Terms

Unless the context clearly requires otherwise, throughout the description and the claims, the following applies:

In general, unless otherwise indicated, singular elements may be in the plural and vice versa with no loss of generality. The use of the masculine can refer to masculine, feminine or both.

The terms "comprise", "comprising" and the like are to be construed in an inclusive sense, as opposed to an exclusive or exhaustive sense, that is to say, in the sense of "including, but not limited to".

The terms "connected", "coupled", or any variant thereof, means any connection or coupling, either direct or indirect, between two or more elements; the coupling or connection between the elements can be physical, logical, or a combination thereof.

The words "herein," "above," "below" and words of similar import, when used in this application, refer to this application as a whole and not to any particular portions of this application.

The word "or" in reference to a list of two or more items covers all of the following interpretations of the word: any of the items in the list, all of the items in the list and any combination of the items in the list.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the examples described and illustrated. The subject matter described herein may assume various alternative orientations. Accordingly, these directional terms are not strictly defined and should not be interpreted narrowly.

To aid the Patent Office and any readers of any patent issued on this application in interpreting the claims appended hereto, applicant wishes to note that they do not intend any of the appended claims or claim elements to invoke 35 U.S.C. 112(f) unless the words "means for" or "step for" are explicitly used in the particular claim.

D. Claim Support

Disclosed herein is a method for defining cut lines to generate a three dimensional ("3D") representation of a fetus, the method comprising: acquiring a plurality of ultrasound frames of the fetus using an ultrasound scanner in an arbitrary orientation with respect to the fetus; and processing, by a processor, each ultrasound frame of the plurality of ultrasound frames against an artificial intelligence ("AI") model to predict a different cut line on the ultrasound frame, wherein each cut line is positioned exterior to an image of the fetus appearing on the ultrasound frame; using the different cut lines on the plurality of ultrasound frames to generate the 3D representation of the fetus.

In some embodiments, the method is performed without manual input of a region of interest on any of the acquired plurality of ultrasound frames.

In some embodiments, the AI model is trained with a plurality of training ultrasound frames each having a labeled cut line that is positioned relative to an imaged fetus in the training ultrasound frame.

In some embodiments, at least some of the labeled cut lines are defined using manual input.

In some embodiments, a cut line on the training ultrasound frame is labeled as acceptable if all points on the cut line are positioned exterior to the imaged fetus in the training ultrasound frame and all points on the cut line are positioned exterior to an imaged placenta, uterine wall, amniotic sac, umbilical cord, cervix, and bladder.

In some embodiments, a cut line on the training ultrasound frame is labeled as acceptable if all points on the cut line are positioned within amniotic fluid imaged in the training ultrasound frame.

In some embodiments, a cut line on the training ultrasound frame is labeled as unacceptable if any point on the cut line is positioned on or interior to the imaged fetus in the training ultrasound frame or any point on the cut line is positioned on or interior to an imaged placenta, uterine wall, amniotic sac, umbilical cord, cervix, or bladder.

In some embodiments, when using the different cut lines on the plurality of ultrasound frames to generate the 3D representation of the fetus, the method further comprises: removing, from each of the ultrasound frames, ultrasound data on a distal side of the cut line relative to the image of the fetus appearing on the ultrasound frame; and using ultrasound data that remains in each of the plurality of ultrasound frames to generate the 3D representation of the fetus.

In some embodiments, when using the different cut lines on the plurality of ultrasound frames to generate the 3D representation of the fetus, the method further comprises using ultrasound data on a proximal side of the cut line relative to the image of the fetus appearing on the ultrasound frame to generate the 3D representation.

In some embodiments, the method comprises determining, during the processing step, a confidence level for each of the predicted cut lines; wherein when using the different cut lines on the plurality of ultrasound frames to generate the 3D representation of the fetus, the method further comprises: removing, from each of the plurality of ultrasound frames for which the confidence level is above a threshold, ultrasound data on a distal side of the cut line relative to the image of the fetus appearing on the ultrasound data frame; and using remaining ultrasound data in each of the ultrasound frames from which ultrasound data has been removed to generate the 3D representation.

In some embodiments, the method comprises repeating the acquiring, processing, and using steps for subsequently acquired ultrasound frames of the fetus, wherein the 3D representation is projected onto a real time image.

In some embodiments, the predicted cut lines on the plurality of ultrasound frames are each positioned within imaged amniotic fluid that surrounds the fetus.

In some embodiments, the predicted cut lines on the plurality of ultrasound frames are each positioned interior to an imaged uterus that surrounds the fetus.

In some embodiments, the predicted cut lines each comprise a Bézier curve, a polynomial curve, a spline curve, a freeform curve, a parametric curve, or a selection of two or more therefrom.

In some embodiments, the plurality of ultrasound frames of the fetus contain imaged fetal anatomy, the fetal anatomy comprising a face, a head, an ear, a nose, an eye, a neck, a torso, a foot, a leg, a hand, an arm, or a selection of two or more therefrom.

In some embodiments, the fetus is positioned adjacent to a wall of an amniotic sac, and the predicted cut lines on the plurality of ultrasound frames delineate the fetus from the wall of the amniotic sac.

In some embodiments, when using the different cut lines on the plurality of ultrasound frames to generate the 3D representation of the fetus, the method further comprises removing, from one or more of the ultrasound frames, data representing an imaged umbilical cord.

In some embodiments, the ultrasound scanner is held steadily in the arbitrary orientation by an operator of the ultrasound scanner while a motor in the ultrasound scanner tilts a transducer in the ultrasound scanner so that each of the plurality of ultrasound frames is acquired at a different angle of the transducer.

In some embodiments, the method comprises labeling each of the predicted cut lines as either acceptable or unacceptable, with at least one of the predicted cut lines being labeled as unacceptable; and using the ultrasound frames with labeled cut lines for training or reinforcing the AI model.

In some embodiments, the method comprises determining, by a processor, a physical dimension of the fetus using the 3D model of the fetus; and calculating an age of the fetus using the physical dimension.

In some embodiments, the method is performed without human input to measure the physical dimension.

In some embodiments, the physical dimension comprises one or more of: crown rump length (CRL), biparietal diameter (BPD), head circumference (HC), abdominal circumference (AC), femur length (FL), cephalic index (CI), humerus length (HL), Binocular Distance (BOD), or Intraocular Diameter (IOD).

Also disclosed herein is an ultrasound system for generating a three dimensional ("3D") representation of a fetus, the system comprising an ultrasound scanner configured to acquire a plurality of ultrasound frames of the fetus with the ultrasound scanner in an arbitrary orientation with respect to the fetus; and a processor configured to: process each ultrasound frame of the plurality of ultrasound frames against an artificial intelligence ("AI") model to predict a different cut line on the ultrasound frame, wherein each cut line is positioned exterior to an image of the fetus appearing on the ultrasound frame; and use the different cut lines on the plurality of ultrasound frames to generate the 3D representation of the fetus.

In some embodiments, the processor is configured to generate the 3D representation of the fetus without manual input of a region of interest on any of the acquired plurality of ultrasound frames.

In some embodiments, the AI model is trained with a plurality of training ultrasound frames each having a labeled cut line that is positioned relative to an imaged fetus in the training ultrasound frame.

In some embodiments, at least some of the labeled cut lines are defined using manual input.

In some embodiments, a cut line on the training ultrasound frame is labeled as acceptable if all points on the cut line are positioned exterior to the imaged fetus in the training ultrasound frame and all points on the cut line are positioned exterior to an imaged placenta, uterine wall, amniotic sac, umbilical cord, cervix, and bladder.

In some embodiments, a cut line on the training ultrasound frame is labeled as acceptable if all points on the cut line are positioned within amniotic fluid imaged in the training ultrasound frame.

In some embodiments, a cut line on the training ultrasound frame is labeled as unacceptable if any point on the cut line is positioned on or interior to the imaged fetus in the training ultrasound frame or any point on the cut line is positioned on or interior to an imaged placenta, uterine wall, amniotic sac, umbilical cord, cervix, or bladder.

In some embodiments, when using the different cut lines on the plurality of ultrasound frames to generate the 3D representation of the fetus, the processor is further configured to remove, from each of the ultrasound frames, ultrasound data on a distal side of the cut line relative to the image of the fetus appearing on the ultrasound frame; and use ultrasound data that remains in each of the plurality of ultrasound frames to generate the 3D representation of the fetus.

In some embodiments, when using the different cut lines on the plurality of ultrasound frames to generate the 3D representation of the fetus, the processor is further configured to use ultrasound data on a proximal side of the cut line relative to the image of the fetus appearing on the ultrasound frame to generate the 3D representation.

In some embodiments, the processor is further configured to determine, during the processing step, a confidence level for each of the predicted cut lines; and wherein when using the different cut lines on the plurality of ultrasound frames to generate the 3D representation of the fetus, the processor is further configured to: remove, from each of the plurality of ultrasound frames for which the confidence level is above a threshold, ultrasound data on a distal side of the cut line relative to the image of the fetus appearing on the ultrasound data frame; and use remaining ultrasound data in each of the ultrasound frames from which ultrasound data has been removed to generate the 3D representation.

In some embodiments, the ultrasound scanner and processor are further configured to repeatedly generate the 3D representation and project it onto a real time image.

In some embodiments, the predicted cut lines on the plurality of ultrasound frames are each positioned within imaged amniotic fluid that surrounds the fetus.

In some embodiments, the predicted cut lines on the plurality of ultrasound frames are each positioned interior to an imaged uterus that surrounds the fetus.

In some embodiments, the predicted cut lines each comprise a Bézier curve, a polynomial curve, a spline curve, a freeform curve, a parametric curve, or a selection of two or more therefrom.

In some embodiments, the plurality of ultrasound frames of the fetus contain imaged fetal anatomy, the fetal anatomy comprising a face, a head, an ear, a nose, an eye, a neck, a torso, a foot, a leg, a hand, an arm, or a selection of two or more therefrom.

In some embodiments, the fetus is positioned adjacent to a wall of an amniotic sac, and the predicted cut lines on the plurality of ultrasound frames delineate the fetus from the wall of the amniotic sac.

In some embodiments, when using the different cut lines on the plurality of ultrasound frames to generate the 3D representation of the fetus, the processor is further configured to remove, from one or more of the ultrasound frames, data representing an imaged umbilical cord.

In some embodiments, the ultrasound scanner comprises a motor in the ultrasound scanner that tilts a transducer in the ultrasound scanner so that each of the plurality of ultrasound frames is acquired at a different angle of the transducer, while the ultrasound scanner is held steadily in the arbitrary orientation by an operator of the ultrasound scanner.

In some embodiments, the processor is further configured to label each of the predicted cut lines as either acceptable or unacceptable, with at least one of the predicted cut lines being labeled as unacceptable; and use the ultrasound frames with labeled cut lines for training or reinforcing the AI model.

In some embodiments, the processor is further configured to determine a physical dimension of the fetus using the 3D model of the fetus; and calculate an age of the fetus using the physical dimension.

In some embodiments, the processor is further configured to determine the physical dimension and calculate the age without human input to measure the physical dimension.

In some embodiments, the physical dimension comprises one or more of: crown rump length (CRL), biparietal diameter (BPD), head circumference (HC), abdominal circumference (AC), femur length (FL), cephalic index (CI), humerus length (HL), Binocular Distance (BOD), or Intraocular Diameter (IOD).

Still further disclosed is a non-transient computer-readable media storing computer-readable instructions, which, when executed by a processor cause the processor to receive a plurality of ultrasound frames of a fetus from an ultrasound scanner in an arbitrary orientation with respect to the fetus; process each ultrasound frame of the plurality of ultrasound frames against an artificial intelligence ("AI") model to predict a different cut line on the ultrasound frame, wherein each cut line is positioned exterior to an image of the fetus appearing on the ultrasound frame; and use the different cut lines on the plurality of ultrasound frames to generate a 3D representation of the fetus.

In some embodiments, the computer-readable instructions further cause the processor to generate the 3D representation of the fetus without manual input of a region of interest on any of the acquired plurality of ultrasound frames.

In some embodiments, the AI model is trained with a plurality of training ultrasound frames each having a labeled cut line that is positioned relative to an imaged fetus in the training ultrasound frame.

In some embodiments, at least some of the labeled cut lines are defined using manual input.

In some embodiments, a cut line on the training ultrasound frame is labeled as acceptable if all points on the cut line are positioned exterior to the imaged fetus in the training ultrasound frame and all points on the cut line are positioned exterior to an imaged placenta, uterine wall, amniotic sac, umbilical cord, cervix, and bladder.

In some embodiments, a cut line on the training ultrasound frame is labeled as acceptable if all points on the cut line are positioned within amniotic fluid imaged in the training ultrasound frame.

In some embodiments, a cut line on the training ultrasound frame is labeled as unacceptable if any point on the cut line is positioned on or interior to the imaged fetus in the training ultrasound frame or any point on the cut line is positioned on or interior to an imaged placenta, uterine wall, amniotic sac, umbilical cord, cervix, or bladder.

In some embodiments, when using the different cut lines on the plurality of ultrasound frames to generate the 3D representation of the fetus, the computer-readable instructions further cause the processor to: remove, from each of the ultrasound frames, ultrasound data on a distal side of the cut line relative to the image of the fetus appearing on the ultrasound frame; and use ultrasound data that remains in each of the plurality of ultrasound frames to generate the 3D representation of the fetus.

In some embodiments, when using the different cut lines on the plurality of ultrasound frames to generate the 3D representation of the fetus, the computer-readable instructions further cause the processor to: use ultrasound data on a proximal side of the cut line relative to the image of the fetus appearing on the ultrasound frame to generate the 3D representation.

In some embodiments, the computer-readable instructions further cause the processor to: determine, during the processing step, a confidence level for each of the predicted cut lines; and wherein when using the different cut lines on the plurality of ultrasound frames to generate the 3D representation of the fetus, cause the processor to: remove, from each of the plurality of ultrasound frames for which the confidence level is above a threshold, ultrasound data on a distal side of the cut line relative to the image of the fetus appearing on the ultrasound data frame; and use remaining ultrasound data in each of the ultrasound frames from which ultrasound data has been removed to generate the 3D representation.

In some embodiments, the computer-readable instructions further cause the processor to repeatedly generate the 3D representation and project it onto a real time image.

In some embodiments, the predicted cut lines on the plurality of ultrasound frames are each positioned within imaged amniotic fluid that surrounds the fetus.

In some embodiments, the predicted cut lines on the plurality of ultrasound frames are each positioned interior to an imaged uterus that surrounds the fetus.

In some embodiments, the predicted cut lines each comprise a Bézier curve, a polynomial curve, a spline curve, a freeform curve, a parametric curve, or a selection of two or more therefrom.

In some embodiments, the plurality of ultrasound frames of the fetus contain imaged fetal anatomy, the fetal anatomy comprising a face, a head, an ear, a nose, an eye, a neck, a torso, a foot, a leg, a hand, an arm, or a selection of two or more therefrom.

In some embodiments, the fetus is positioned adjacent to a wall of an amniotic sac, and the predicted cut lines on the plurality of ultrasound frames delineate the fetus from the wall of the amniotic sac.

In some embodiments, when using the different cut lines on the plurality of ultrasound frames to generate the 3D representation of the fetus, the computer-readable instructions further cause the processor to remove, from one or more of the ultrasound frames, data representing an imaged umbilical cord.

In some embodiments, the computer-readable instructions further cause the processor to control a motor in the ultrasound scanner to tilts a transducer in the ultrasound scanner so that each of the plurality of ultrasound frames is acquired at a different angle of the transducer, while the ultrasound scanner is held steadily in the arbitrary orientation by an operator of the ultrasound scanner.

In some embodiments, the computer-readable instructions further cause the processor to: label each of the predicted cut lines as either acceptable or unacceptable, with at least one of the predicted cut lines being labeled as unacceptable; and use the ultrasound frames with labeled cut lines for training or reinforcing the AI model.

In some embodiments, the computer-readable instructions further cause the processor to: determine a physical dimension of the fetus using the 3D model of the fetus; and calculate an age of the fetus using the physical dimension.

In some embodiments, the computer-readable instructions further cause the processor to determine the physical dimension and calculate the age without human input to measure the physical dimension.

In some embodiments, the physical dimension comprises one or more of: crown rump length (CRL), biparietal diameter (BPD), head circumference (HC), abdominal circumference (AC), femur length (FL), cephalic index (CI), humerus length (HL), Binocular Distance (BOD), or Intraocular Diameter (IOD).

The invention claimed is:

1. A method for defining cut lines to generate a three-dimensional ("3D") representation of a fetus, the method comprising:
    acquiring a plurality of two-dimensional ("2D") ultrasound frames of the fetus using an ultrasound scanner in an arbitrary orientation with respect to the fetus;
    processing, by a processor, each 2D acquired ultrasound frame of the plurality of 2D acquired ultrasound frames against an artificial intelligence ("AI") model, the AI Model being trained with a plurality of 2D training ultrasound frames each frame being on a plane, as scanned, and each having a training cut line thereon, wherein a training cut line on a 2D training ultrasound frame is labeled as acceptable if all points on the training cut line are positioned around a fetal body part of the fetus imaged in the plane of the 2D training ultrasound frame, wherein the processing of the 2D acquired ultrasound frame against the AI model is to predict a cut line (predicted cut line) on each of the 2D acquired ultrasound frames; and
    using the different predicted cut lines on the plurality of 2D acquired ultrasound frames to generate the 3D representation of the fetus.

2. The method of claim 1, wherein the AI model is trained with a further plurality of 2D training ultrasound frames and each 2D training ultrasound frame of the further plurality of 2D training ultrasound frames has a labeled training cut line that is positioned relative to an imaged fetus in the 2D training ultrasound frame, the imaged fetus being different from the fetus in the plurality of 2D acquired ultrasound frames.

3. The method of claim 1, wherein a training cut line on each 2D training ultrasound frame of the further plurality of 2D training ultrasound frames is labeled as acceptable if all points on the training cut line are positioned exterior to the imaged fetus in the 2D training ultrasound frame and all points on the training cut line are positioned exterior to an imaged placenta, uterine wall, amniotic sac, umbilical cord, cervix, and bladder.

4. The method of claim 1, wherein when using the different predicted cut lines on the plurality of 2D acquired ultrasound frames to generate the 3D representation of the fetus, the method further comprises:
    removing, from each of the 2D acquired ultrasound frames, ultrasound data on a distal side of the cut line relative to the image of the fetus appearing on the 2D acquired ultrasound frame; and
    using ultrasound data that remains in each of the plurality of 2D acquired ultrasound frames to generate the 3D representation of the fetus.

5. The method of claim 1, wherein when using the different predicted cut lines on the plurality of 2D acquired ultrasound frames to generate the 3D representation of the fetus, the method further comprises:
    using ultrasound data on a proximal side of the cut line relative to the image of the fetus appearing on the 2D acquired ultrasound frame to generate the 3D representation of the fetus.

6. The method of claim 1, further comprising:
    determining, during the processing step, a confidence level for each of the predicted cut lines; and
    wherein when using the different predicted cut lines on the plurality of 2D acquired ultrasound frames to generate the 3D representation of the fetus, the method further comprises:
        removing, from each of the plurality of 2D acquired ultrasound frames for which the confidence level is above a threshold, ultrasound data on a distal side of the cut line relative to the image of the fetus appearing on the 2D acquired ultrasound frame; and
        using remaining ultrasound data in each of the 2D acquired ultrasound frames from which ultrasound data has been removed to generate the 3D representation of the fetus.

7. The method of claim 1, comprising:
    repeating the acquiring, processing, and using steps for subsequently acquired 2D acquired ultrasound frames of the fetus, wherein the 3D representation is projected onto a real time image.

8. The method of claim 1, wherein the predicted cut lines each comprise a Bézier curve, a polynomial curve, a spline curve, a freeform curve, a parametric curve, or a selection of two or more therefrom.

9. The method of claim 1, wherein the fetal body part is a skeletal/bone structure.

10. The method of claim 1, wherein the ultrasound scanner is held steadily in the arbitrary orientation by an operator of the ultrasound scanner while a motor in the ultrasound scanner tilts a transducer in the ultrasound scanner so that each of the plurality of 2D acquired ultrasound frames is acquired at a different angle of the transducer.

11. An ultrasound system for generating a three-dimensional ("3D") representation of a fetus, the system comprising:
    an ultrasound scanner configured to acquire a plurality of two-dimensional ("2D") acquired ultrasound frames of the fetus with the ultrasound scanner in an arbitrary orientation with respect to the fetus; and
    a processor configured to:
        process each 2D acquired ultrasound frame of the plurality of 2D acquired ultrasound frames against an artificial intelligence ("AI") model, the AI model being trained with a plurality of 2D training ultrasound frames each frame being on a plane, as scanned, and each having a training cut line thereon, wherein a 2D training ultrasound frame wherein a training cut line on a 2D training ultrasound frame is labeled as acceptable if all points on the training cut line are positioned around a fetal body part of the fetus imaged in the plane of the 2D training ultrasound frame, wherein the processing of the 2D acquired ultrasound frame against the AI model is to predict a cut line (predicted cut line) on each of the 2D acquired ultrasound frames; and use the different predicted cut lines on the plurality of 2D acquired ultrasound frames to generate the 3D representation of the fetus.

12. The ultrasound system of claim 11, wherein the AI model is trained with a further plurality of 2D training ultrasound frames and each 2D training ultrasound frame of the further plurality of 2D training ultrasound frames has a labeled training cut line that is positioned relative to an imaged fetus in the 2D training ultrasound frame, the imaged fetus being different from the fetus in the acquired plurality of 2D acquired ultrasound frames.

13. The ultrasound system of claim 11, wherein a training cut line on each 2D training ultrasound frame of the further plurality of 2D training ultrasound frames is labeled as acceptable if all points on the training cut line are positioned exterior to the imaged fetus in the 2D training ultrasound frame and all points on the training cut line are positioned exterior to an imaged placenta, uterine wall, amniotic sac, umbilical cord, cervix, and bladder.

14. The ultrasound system of claim 11, wherein when using the different predicted cut lines on the plurality of 2D acquired ultrasound frames to generate the 3D representation of the fetus, the processor is further configured to:

remove, from each of the 2D acquired ultrasound frames, ultrasound data on a distal side of the cut line relative to the image of the fetus appearing on the 2D acquired ultrasound frame; and use ultrasound data that remains in each of the plurality of 2D acquired ultrasound frames to generate the 3D representation of the fetus.

15. The ultrasound system of claim 11, wherein when using the different predicted cut lines on the plurality of 2D acquired ultrasound frames to generate the 3D representation of the fetus, the processor is further configured to:

use ultrasound data on a proximal side of the cut line relative to the image of the fetus appearing on the 2D acquired ultrasound frame to generate the 3D representation.

16. The ultrasound system of claim 11, wherein the processor is further configured to:

determine, during the processing step, a confidence level for each of the predicted cut lines; and wherein when using the different predicted cut lines on the plurality of 2D acquired ultrasound frames to generate the 3D representation of the fetus, the processor is further configured to:

remove, from each of the plurality of 2D acquired ultrasound frames for which the confidence level is above a threshold, ultrasound data on a distal side of the cut line relative to the image of the fetus appearing on the 2D acquired ultrasound frame; and use remaining ultrasound data in each of the 2D acquired ultrasound frames from which ultrasound data has been removed to generate the 3D representation.

17. The ultrasound system of claim 11, wherein the ultrasound scanner and processor are further configured to:

repeatedly generate the 3D representation and project it onto a real time image.

18. A non-transitory computer-readable media storing computer-readable instructions, which, when executed by a processor cause the processor to:

receive a plurality of two-dimensional ("2D") acquired ultrasound frames of a fetus from an ultrasound scanner in an arbitrary orientation with respect to the fetus;

process each 2D acquired ultrasound frame of the plurality of 2D acquired ultrasound frames against an artificial intelligence ("AI") model, the AI model being trained with a plurality of 2D training ultrasound frames each frame being on a plane, as scanned, and each having a training cut line thereon, wherein a training cut line on a 2D training ultrasound frame is labeled as acceptable if all points on the training cut line are positioned around a fetal body part of the fetus imaged in the plane of the 2D training ultrasound frame, wherein the processing of the 2D acquired ultrasound frame against the AI model to predict a cut line (predicted cut line) on each of the 2D acquired ultrasound frames; and use the different predicted cut lines on the plurality of 2D acquired ultrasound frames to generate a three-dimensional (3D) representation of the fetus.

19. The non-transitory computer-readable media of claim 18, wherein the AI model is trained with a further plurality of 2D training ultrasound frames and each 2D training ultrasound frame of the further plurality of 2D training ultrasound frames has a labeled training cut line that is positioned relative to an imaged fetus in the 2D training ultrasound frame, the imaged fetus being different from the fetus in the acquired plurality of 2D acquired ultrasound frames.

20. The non-transitory computer-readable media of claim 19, wherein a training cut line on each 2D training ultrasound frame of the further plurality of 2D training ultrasound frames is labeled as acceptable if all points on the training cut line are positioned exterior to the imaged fetus in the 2D training ultrasound frame and all points on the training cut line are positioned exterior to an imaged placenta, uterine wall, amniotic sac, umbilical cord, cervix, and bladder.

* * * * *